(12) United States Patent
DiPoto et al.

(10) Patent No.: US 10,575,882 B2
(45) Date of Patent: Mar. 3, 2020

(54) DISTAL TIP FOR BONE FIXATION DEVICES

(71) Applicant: IlluminOss Medical, Inc., East Providence, RI (US)

(72) Inventors: Gene P. DiPoto, Upton, MA (US); Robert A. Rabiner, Barrington, RI (US); Jeffrey P. Brousseau, Barrington, RI (US); Anthony W. O'Leary, Walpole, MA (US); Chi Y. Wong, Canton, MA (US); Augustus C. Shanahan, Newton, MA (US); Nicholas Ferrer, West Greenwich, RI (US); John Unger, Wrentham, MA (US)

(73) Assignee: IlluminOss Medical, Inc., East Providence, RI (US)

( * ) Notice: Subject to any disclaimer, the term of this patent is extended or adjusted under 35 U.S.C. 154(b) by 0 days.

(21) Appl. No.: 15/603,771

(22) Filed: May 24, 2017

(65) Prior Publication Data

US 2017/0252077 A1    Sep. 7, 2017

Related U.S. Application Data

(63) Continuation of application No. 13/796,085, filed on Mar. 12, 2013, now Pat. No. 9,687,281.

(Continued)

(51) Int. Cl.
*A61B 17/72* (2006.01)
*A61B 17/88* (2006.01)
(Continued)

(52) U.S. Cl.
CPC ...... *A61B 17/7275* (2013.01); *A61B 17/8855* (2013.01); *A61B 17/7097* (2013.01);
(Continued)

(58) Field of Classification Search
CPC ...... A61B 17/72–7291; A61B 17/7097; A61B 17/8802–8827; A61B 17/8833; A61B 2017/00898
See application file for complete search history.

(56) References Cited

U.S. PATENT DOCUMENTS

| | | | |
|---|---|---|---|
| 3,485,520 | A | 12/1969 | Alexander |
| 4,271,839 | A | 6/1981 | Fogarty et al. |

(Continued)

FOREIGN PATENT DOCUMENTS

| | | |
|---|---|---|
| DE | 40 28 466 | 3/1992 |
| EP | 0 709 698 | 5/1996 |

(Continued)

OTHER PUBLICATIONS

Jovanovic et al., "Fixion Nails for Humeral Fractures, Injury", Int. J. Care Injured, vol. 35, Issue 11, pp. 1140-1142, Nov. 2004.

(Continued)

*Primary Examiner* — Nicholas J Plionis
*Assistant Examiner* — Steven J Cotroneo
(74) *Attorney, Agent, or Firm* — Greenberg Traurig, LLP; David J. Dykeman; Roman Fayerberg

(57) ABSTRACT

Distal tip designs for bone fixation devices are disclosed. In some embodiments, a system for bone fixation includes a delivery catheter having a proximal end and a distal end; an expandable member having a proximal region and a distal region, wherein the expandable member is releasably attached about the distal end of the delivery catheter at the proximal region of the expandable member; a distal cap attached to the distal region of the expandable member to seal the expandable member; a light conducting fiber; and a light-sensitive liquid; wherein the delivery catheter has an inner void for passage of a light-sensitive liquid into the expandable member to expand the expandable member and (Continued)

an inner lumen for passage of the light conducting fiber into the expandable member to cure the light-sensitive liquid inside the expandable member.

16 Claims, 11 Drawing Sheets

Related U.S. Application Data

(60) Provisional application No. 61/739,972, filed on Dec. 20, 2012.

(51) Int. Cl.
    *A61B 17/70*           (2006.01)
    *A61B 90/30*           (2016.01)
    *A61B 90/00*           (2016.01)
    *A61N 5/06*            (2006.01)

(52) U.S. Cl.
    CPC . *A61B 2090/306* (2016.02); *A61B 2090/3966* (2016.02); *A61N 5/0601* (2013.01); *A61N 2005/063* (2013.01)

(56) References Cited

U.S. PATENT DOCUMENTS

| | | |
|---|---|---|
| 4,280,233 A | 7/1981 | Raab |
| 4,294,251 A | 10/1981 | Greenwald et al. |
| 4,313,434 A | 2/1982 | Segal |
| 4,341,691 A | 7/1982 | Anuta |
| 4,369,772 A | 1/1983 | Miller |
| 4,414,608 A | 11/1983 | Furihata |
| 4,422,719 A | 12/1983 | Orcutt |
| 4,433,898 A | 2/1984 | Nasiri |
| 4,462,394 A | 7/1984 | Jacobs |
| 4,466,435 A | 8/1984 | Murray |
| 4,562,598 A | 1/1986 | Kranz |
| 4,686,973 A | 8/1987 | Frisch |
| 4,697,584 A | 10/1987 | Haynes |
| 4,735,625 A | 4/1988 | Davidson |
| 4,870,953 A | 10/1989 | DonMichael et al. |
| 4,888,024 A | 12/1989 | Powlan |
| 4,892,550 A | 1/1990 | Huebsch |
| 4,904,391 A | 2/1990 | Freeman |
| 4,961,424 A | 10/1990 | Kubota et al. |
| 4,963,151 A | 10/1990 | Ducheyne et al. |
| 4,969,888 A | 11/1990 | Scholten et al. |
| 5,030,093 A | 7/1991 | Mitnick |
| 5,049,157 A | 9/1991 | Mittelmeier et al. |
| 5,085,660 A | 2/1992 | Lin |
| 5,092,899 A | 3/1992 | Forte |
| 5,102,413 A | 4/1992 | Poddar |
| 5,108,404 A | 4/1992 | Scholten et al. |
| 5,112,333 A | 5/1992 | Fixel |
| 5,207,669 A | 5/1993 | Baker et al. |
| 5,222,958 A | 6/1993 | Chin |
| 5,295,733 A | 3/1994 | LeBegue |
| 5,295,962 A | 3/1994 | Crocker et al. |
| 5,303,718 A | 4/1994 | Krajicek |
| 5,316,550 A | 5/1994 | Forte |
| 5,336,699 A | 8/1994 | Cooke et al. |
| 5,372,598 A | 12/1994 | Luhr et al. |
| 5,376,123 A | 12/1994 | Klaue et al. |
| 5,391,144 A | 2/1995 | Sakurai et al. |
| 5,415,654 A | 5/1995 | Daikuzono |
| 5,423,850 A | 6/1995 | Berger |
| 5,432,876 A | 7/1995 | Appeldorn et al. |
| 5,443,468 A | 8/1995 | Johnson |
| 5,445,608 A | 8/1995 | Chen et al. |
| 5,462,552 A | 10/1995 | Kiester |
| 5,480,400 A * | 1/1996 | Berger ............... A61B 17/7225 604/96.01 |
| 5,538,514 A | 7/1996 | Hawkins |
| 5,548,676 A | 8/1996 | Savage, Jr. |
| 5,554,111 A | 9/1996 | Morrey et al. |
| 5,556,429 A | 9/1996 | Felt |
| 5,571,204 A | 11/1996 | Nies |
| 5,658,310 A | 8/1997 | Berger |
| 5,658,963 A | 8/1997 | Qian et al. |
| 5,702,446 A | 12/1997 | Schenck et al. |
| 5,705,181 A | 1/1998 | Cooper et al. |
| 5,707,374 A | 1/1998 | Schmidt |
| 5,713,901 A | 2/1998 | Tock |
| 5,795,353 A | 8/1998 | Felt |
| 5,824,087 A | 10/1998 | Aspden et al. |
| 5,827,289 A | 10/1998 | Reiley et al. |
| 5,888,220 A | 3/1999 | Felt et al. |
| 5,897,557 A | 4/1999 | Chin et al. |
| 5,908,433 A | 6/1999 | Eager et al. |
| 5,930,424 A | 7/1999 | Heimberger et al. |
| 5,972,015 A | 10/1999 | Scribner et al. |
| 5,980,075 A | 11/1999 | Sheaffer |
| 5,980,253 A | 11/1999 | Oxman et al. |
| 5,987,199 A | 11/1999 | Zarian et al. |
| 5,989,230 A | 11/1999 | Frassica |
| 5,997,570 A | 12/1999 | Ligtenberg et al. |
| 6,008,264 A | 12/1999 | Ostler |
| 6,019,761 A | 2/2000 | Gustilo |
| 6,019,774 A | 2/2000 | Weiss et al. |
| 6,033,411 A | 3/2000 | Preissman |
| 6,039,762 A | 3/2000 | McKay |
| 6,042,380 A | 3/2000 | De Rowe |
| 6,048,346 A | 4/2000 | Reiley et al. |
| 6,053,917 A | 4/2000 | Sherman et al. |
| 6,059,789 A | 5/2000 | Dinger et al. |
| 6,066,154 A | 5/2000 | Reiley et al. |
| 6,077,265 A | 6/2000 | Werding et al. |
| 6,079,868 A | 6/2000 | Rydell |
| 6,103,203 A | 8/2000 | Fischer |
| 6,110,176 A | 8/2000 | Shapira |
| 6,121,341 A | 9/2000 | Sawhney et al. |
| 6,127,597 A | 10/2000 | Beyar et al. |
| 6,136,011 A | 10/2000 | Stambaugh |
| 6,140,452 A | 10/2000 | Felt et al. |
| 6,159,236 A | 12/2000 | Biel |
| 6,179,852 B1 | 1/2001 | Strickland et al. |
| 6,195,477 B1 | 2/2001 | Denuto et al. |
| 6,200,134 B1 | 3/2001 | Kovac et al. |
| 6,217,581 B1 | 4/2001 | Tolson |
| 6,223,085 B1 | 4/2001 | Dann et al. |
| 6,224,630 B1 | 5/2001 | Bao et al. |
| 6,235,043 B1 * | 5/2001 | Reiley ............... A61B 17/7097 604/101.01 |
| 6,241,734 B1 | 6/2001 | Scribner et al. |
| 6,248,110 B1 | 6/2001 | Reiley et al. |
| 6,248,131 B1 | 6/2001 | Felt et al. |
| 6,254,571 B1 | 7/2001 | Hart |
| 6,258,089 B1 | 7/2001 | Campbell et al. |
| 6,261,289 B1 | 7/2001 | Levy |
| 6,280,456 B1 | 8/2001 | Scribner et al. |
| 6,282,013 B1 | 8/2001 | Ostler et al. |
| 6,290,382 B1 | 9/2001 | Bourn et al. |
| 6,299,597 B1 | 10/2001 | Buscemi et al. |
| 6,306,177 B1 | 10/2001 | Felt et al. |
| 6,319,255 B1 | 11/2001 | Grundei et al. |
| 6,332,894 B1 | 12/2001 | Stalcup et al. |
| 6,336,914 B1 | 1/2002 | Gillespie, III |
| 6,336,930 B1 | 1/2002 | Stalcup et al. |
| 6,358,252 B1 | 3/2002 | Shapira |
| 6,387,098 B1 | 5/2002 | Cole et al. |
| 6,395,007 B1 | 5/2002 | Bhatnagar et al. |
| 6,416,531 B2 | 7/2002 | Chen |
| 6,416,737 B1 | 7/2002 | Manolagas et al. |
| 6,419,483 B1 | 7/2002 | Adam et al. |
| 6,423,055 B1 | 7/2002 | Farr et al. |
| 6,423,083 B2 | 7/2002 | Reiley et al. |
| 6,425,923 B1 | 7/2002 | Stalcup et al. |
| 6,440,444 B2 | 8/2002 | Boyce et al. |
| 6,443,988 B2 | 9/2002 | Felt et al. |
| 6,447,514 B1 | 9/2002 | Stalcup et al. |
| 6,458,375 B1 | 10/2002 | Gertzman et al. |
| 6,478,751 B1 | 11/2002 | Krueger et al. |
| 6,482,234 B1 | 11/2002 | Weber et al. |

(56) References Cited

U.S. PATENT DOCUMENTS

| | | | |
|---|---|---|---|
| 6,485,512 B1 | 11/2002 | Cheng | |
| 6,494,883 B1 | 12/2002 | Ferree | |
| 6,524,251 B2 | 2/2003 | Rabiner et al. | |
| 6,524,313 B1 | 2/2003 | Fassier et al. | |
| 6,551,321 B1 | 4/2003 | Burkinshaw et al. | |
| 6,551,337 B1 | 4/2003 | Rabiner et al. | |
| 6,565,528 B1 | 5/2003 | Mueller | |
| 6,579,277 B1 | 6/2003 | Rabiner et al. | |
| 6,579,279 B1 | 6/2003 | Rabiner et al. | |
| 6,605,056 B2 | 8/2003 | Eidenschink et al. | |
| 6,620,185 B1 | 9/2003 | Harvie et al. | |
| 6,623,505 B2 | 9/2003 | Scribner et al. | |
| 6,632,235 B2 | 10/2003 | Weikel et al. | |
| 6,648,881 B2 | 11/2003 | KenKnight et al. | |
| 6,652,547 B2 | 11/2003 | Rabiner et al. | |
| 6,652,587 B2 | 11/2003 | Felt et al. | |
| 6,660,013 B2 | 12/2003 | Rabiner et al. | |
| 6,679,873 B2 | 1/2004 | Rabiner et al. | |
| 6,695,781 B2 | 2/2004 | Rabiner et al. | |
| 6,695,782 B2 | 2/2004 | Rabiner et al. | |
| 6,696,073 B2 | 2/2004 | Boyce et al. | |
| 6,716,216 B1 | 4/2004 | Boucher et al. | |
| 6,719,773 B1 | 4/2004 | Boucher et al. | |
| 6,726,691 B2 | 4/2004 | Osorio et al. | |
| 6,730,048 B1 | 5/2004 | Hare et al. | |
| 6,733,451 B2 | 5/2004 | Rabiner et al. | |
| 6,733,513 B2 | 5/2004 | Boyle et al. | |
| 6,740,093 B2 | 5/2004 | Hochschuler et al. | |
| 6,755,862 B2 | 6/2004 | Keynan | |
| 6,783,530 B1 | 8/2004 | Levy | |
| 6,802,835 B2 | 10/2004 | Rabiner et al. | |
| 6,818,018 B1 | 11/2004 | Sawhney | |
| 6,852,095 B1 | 2/2005 | Ray | |
| 6,866,678 B2 | 3/2005 | Shenderova et al. | |
| 6,869,442 B2 | 3/2005 | Cheng | |
| 6,875,212 B2 | 4/2005 | Shaolian et al. | |
| 6,885,246 B2 | 4/2005 | Tsutsui et al. | |
| 6,887,246 B2 | 5/2005 | Bhatnagar et al. | |
| 6,887,275 B2 | 5/2005 | Carchidi et al. | |
| 6,899,713 B2 * | 5/2005 | Shaolian | A61B 17/1671 606/262 |
| 6,899,719 B2 | 5/2005 | Reiley et al. | |
| 6,932,843 B2 | 8/2005 | Smith et al. | |
| 6,964,667 B2 | 11/2005 | Shaolian et al. | |
| 6,975,898 B2 | 12/2005 | Seibel | |
| 6,979,341 B2 | 12/2005 | Scribner et al. | |
| 6,981,981 B2 | 1/2006 | Reiley et al. | |
| 7,001,431 B2 | 2/2006 | Bao et al. | |
| 7,008,433 B2 | 3/2006 | Voellmicke et al. | |
| 7,048,731 B2 | 5/2006 | Altshuler et al. | |
| 7,052,498 B2 | 5/2006 | Levy et al. | |
| 7,077,865 B2 | 7/2006 | Bao et al. | |
| 7,124,067 B2 | 10/2006 | Ascenzi | |
| 7,141,061 B2 | 11/2006 | Williams et al. | |
| 7,144,414 B2 | 12/2006 | Harvie et al. | |
| 7,153,305 B2 | 12/2006 | Johnson et al. | |
| 7,156,861 B2 | 1/2007 | Scribner et al. | |
| 7,156,880 B2 | 1/2007 | Evans et al. | |
| 7,169,140 B1 | 1/2007 | Kume | |
| 7,215,863 B1 | 5/2007 | Arenella et al. | |
| 7,241,303 B2 | 7/2007 | Reiss et al. | |
| 7,252,677 B2 | 8/2007 | Burwell et al. | |
| 7,258,692 B2 | 8/2007 | Thelen et al. | |
| 7,261,720 B2 | 8/2007 | Stevens et al. | |
| 7,320,709 B2 | 1/2008 | Felt et al. | |
| 7,341,601 B2 | 3/2008 | Eisermann et al. | |
| 7,360,542 B2 | 4/2008 | Nelson et al. | |
| 7,407,616 B2 | 8/2008 | Melikechi et al. | |
| 7,419,450 B2 | 9/2008 | Ito | |
| 7,427,295 B2 | 9/2008 | Ellman et al. | |
| 7,465,318 B2 * | 12/2008 | Sennett | A61B 17/7098 606/92 |
| 7,547,319 B2 | 6/2009 | Segal et al. | |
| 7,621,950 B1 | 11/2009 | Globerman et al. | |
| 7,628,800 B2 | 12/2009 | Sherman et al. | |
| 7,632,277 B2 | 12/2009 | Woll et al. | |
| 7,632,291 B2 | 12/2009 | Stephens et al. | |
| 7,666,205 B2 | 2/2010 | Weikel et al. | |
| 7,722,620 B2 | 5/2010 | Truckai et al. | |
| 7,740,656 B2 | 6/2010 | Mensah et al. | |
| 7,744,555 B2 | 6/2010 | DiMauro et al. | |
| 7,766,965 B2 | 8/2010 | Bao et al. | |
| 7,771,476 B2 | 8/2010 | Justis et al. | |
| 7,776,075 B2 | 8/2010 | Bruneau et al. | |
| 7,806,900 B2 | 10/2010 | Rabiner | |
| 7,811,284 B2 * | 10/2010 | Rabiner | A61B 17/68 606/62 |
| 7,811,286 B2 | 10/2010 | Medoff | |
| 7,811,290 B2 | 10/2010 | Rabiner | |
| 7,842,040 B2 | 11/2010 | Rabiner et al. | |
| 7,850,711 B1 | 12/2010 | Stone et al. | |
| 7,857,748 B2 | 12/2010 | Williams et al. | |
| 7,879,041 B2 * | 2/2011 | Rabiner | A61B 17/7097 606/92 |
| 7,912,539 B2 | 3/2011 | Doty et al. | |
| 7,947,015 B2 | 5/2011 | Herweck et al. | |
| 8,012,157 B2 | 9/2011 | Chang et al. | |
| 8,034,071 B2 | 10/2011 | Scribner et al. | |
| 8,123,807 B2 | 2/2012 | Kim et al. | |
| 8,187,278 B2 | 5/2012 | Biel | |
| 8,210,729 B2 | 7/2012 | O'Leary et al. | |
| 8,211,121 B1 | 7/2012 | Quinn et al. | |
| 8,226,659 B2 | 7/2012 | Rabiner et al. | |
| 8,246,628 B2 | 8/2012 | Rabiner | |
| 8,262,694 B2 | 9/2012 | Widomski et al. | |
| 8,328,402 B2 | 12/2012 | O'Leary et al. | |
| 8,348,956 B2 | 1/2013 | Rabiner | |
| 8,366,711 B2 | 2/2013 | Rabiner et al. | |
| 8,403,968 B2 | 3/2013 | Rabiner et al. | |
| 8,413,664 B2 | 4/2013 | Appling | |
| 8,512,338 B2 * | 8/2013 | Rabiner | A61B 17/7097 606/262 |
| 8,523,901 B2 | 9/2013 | Rabiner et al. | |
| 8,545,499 B2 | 10/2013 | Lozier et al. | |
| 8,574,233 B2 | 11/2013 | Rabiner et al. | |
| 8,668,701 B2 | 3/2014 | Rabiner et al. | |
| 8,672,982 B2 | 3/2014 | Rabiner et al. | |
| 8,684,965 B2 | 4/2014 | Rabiner et al. | |
| 8,708,955 B2 | 4/2014 | Tilson et al. | |
| 8,734,458 B2 | 5/2014 | O'Halloran | |
| 8,734,460 B2 | 5/2014 | Rabiner et al. | |
| 8,764,761 B2 | 7/2014 | Truckai et al. | |
| 8,777,950 B2 | 7/2014 | Colleran et al. | |
| 8,870,965 B2 | 10/2014 | Rabiner et al. | |
| 8,906,030 B2 | 12/2014 | Rabiner et al. | |
| 8,906,031 B2 | 12/2014 | Rabiner et al. | |
| 8,915,966 B2 | 12/2014 | Rabiner et al. | |
| 8,936,382 B2 | 1/2015 | O'Leary et al. | |
| 8,936,644 B2 | 1/2015 | Rabiner et al. | |
| 8,939,977 B2 | 1/2015 | DiPoto et al. | |
| 9,005,254 B2 | 4/2015 | Rabiner et al. | |
| 9,050,079 B2 | 6/2015 | Rabiner et al. | |
| 9,101,419 B2 | 8/2015 | Colleran et al. | |
| 9,125,706 B2 | 9/2015 | Rabiner et al. | |
| 9,144,442 B2 | 9/2015 | Rabiner et al. | |
| 9,179,959 B2 | 11/2015 | Rabiner et al. | |
| 9,216,049 B2 | 12/2015 | Rabiner et al. | |
| 9,254,156 B2 | 2/2016 | Rabiner | |
| 9,254,195 B2 | 2/2016 | Rabiner et al. | |
| 9,265,549 B2 | 2/2016 | Rabiner | |
| 9,427,289 B2 | 8/2016 | Rabiner et al. | |
| 9,433,450 B2 | 9/2016 | Rabiner et al. | |
| 9,687,281 B2 | 6/2017 | DiPoto et al. | |
| 9,717,542 B2 | 8/2017 | Rabiner et al. | |
| 9,724,147 B2 | 8/2017 | Rabiner | |
| 9,775,661 B2 | 10/2017 | Rabiner et al. | |
| 9,855,080 B2 | 1/2018 | Rabiner et al. | |
| 9,855,145 B2 | 1/2018 | Rabiner et al. | |
| 10,111,689 B2 | 10/2018 | Rabiner et al. | |
| 10,292,823 B2 | 5/2019 | Rabiner et al. | |
| 2001/0011174 A1 | 8/2001 | Reiley et al. | |
| 2001/0044626 A1 | 11/2001 | Reiley et al. | |
| 2001/0055462 A1 | 12/2001 | Seibel | |
| 2002/0032444 A1 | 3/2002 | Mische | |

(56) References Cited

U.S. PATENT DOCUMENTS

| | | |
|---|---|---|
| 2002/0082600 A1 | 6/2002 | Shaolian et al. |
| 2002/0091424 A1 | 7/2002 | Biel |
| 2002/0156482 A1 | 10/2002 | Scribner et al. |
| 2002/0161373 A1 | 10/2002 | Osorio et al. |
| 2002/0165544 A1 | 11/2002 | Perren et al. |
| 2002/0198526 A1 | 12/2002 | Shaolian et al. |
| 2003/0028210 A1 | 2/2003 | Boyle et al. |
| 2003/0083642 A1 | 5/2003 | Boyd et al. |
| 2003/0105469 A1 | 6/2003 | Karmon |
| 2003/0114914 A1 | 6/2003 | Cheng |
| 2003/0156431 A1 | 8/2003 | Gozum et al. |
| 2003/0199850 A1 | 10/2003 | Chavez et al. |
| 2003/0212426 A1 | 11/2003 | Olson et al. |
| 2003/0229372 A1 | 12/2003 | Reiley et al. |
| 2004/0006341 A1 | 1/2004 | Shaolian et al. |
| 2004/0024388 A1 | 2/2004 | Altshuler |
| 2004/0034434 A1 | 2/2004 | Evans et al. |
| 2004/0059333 A1 | 3/2004 | Carl et al. |
| 2004/0059417 A1 | 3/2004 | Smith et al. |
| 2004/0092948 A1 | 5/2004 | Stevens et al. |
| 2004/0098015 A1 | 5/2004 | Weikel et al. |
| 2004/0117025 A1 | 6/2004 | Reindel |
| 2004/0133280 A1 | 7/2004 | Trieu |
| 2004/0167561 A1 | 8/2004 | Boucher et al. |
| 2004/0167625 A1 | 8/2004 | Beyar et al. |
| 2004/0225296 A1 | 11/2004 | Reiss et al. |
| 2004/0228142 A1 | 11/2004 | Takada et al. |
| 2004/0230309 A1 | 11/2004 | Di Mauro et al. |
| 2004/0236366 A1* | 11/2004 | Kennedy, II .......... A61M 25/10 606/192 |
| 2004/0247641 A1 | 12/2004 | Felt et al. |
| 2005/0010231 A1 | 1/2005 | Myers |
| 2005/0010297 A1 | 1/2005 | Watson et al. |
| 2005/0015140 A1 | 1/2005 | deBeer |
| 2005/0015148 A1 | 1/2005 | Jansen et al. |
| 2005/0018989 A1 | 1/2005 | Shimizu et al. |
| 2005/0033437 A1 | 2/2005 | Bao et al. |
| 2005/0043733 A1 | 2/2005 | Eisermann et al. |
| 2005/0043808 A1 | 2/2005 | Felt et al. |
| 2005/0049691 A1 | 3/2005 | Mericle et al. |
| 2005/0090901 A1 | 4/2005 | Studer |
| 2005/0119662 A1 | 6/2005 | Reiley et al. |
| 2005/0142315 A1 | 6/2005 | DeSimone et al. |
| 2005/0149022 A1 | 7/2005 | Shaolian et al. |
| 2005/0159749 A1 | 7/2005 | Levy et al. |
| 2005/0171604 A1 | 8/2005 | Michalow |
| 2005/0192671 A1 | 9/2005 | Bao et al. |
| 2005/0197711 A1 | 9/2005 | Cachia |
| 2005/0209629 A1 | 9/2005 | Kerr et al. |
| 2005/0228260 A1 | 10/2005 | Burwell et al. |
| 2005/0234453 A1 | 10/2005 | Shaolian et al. |
| 2005/0251140 A1 | 11/2005 | Shaolian et al. |
| 2005/0284485 A9 | 12/2005 | Nelson et al. |
| 2006/0009550 A1 | 1/2006 | Messersmith et al. |
| 2006/0015105 A1 | 1/2006 | Warren et al. |
| 2006/0036253 A1 | 2/2006 | Leroux et al. |
| 2006/0084985 A1 | 4/2006 | Kim et al. |
| 2006/0100547 A1 | 5/2006 | Rabiner et al. |
| 2006/0100635 A1 | 5/2006 | Reiley et al. |
| 2006/0100706 A1 | 5/2006 | Shadduck et al. |
| 2006/0111726 A1 | 5/2006 | Felt et al. |
| 2006/0122625 A1 | 6/2006 | Truckai et al. |
| 2006/0142747 A1 | 6/2006 | Appling |
| 2006/0155296 A1 | 7/2006 | Richter |
| 2006/0173464 A1 | 8/2006 | Ellman et al. |
| 2006/0183811 A1 | 8/2006 | Melikechi et al. |
| 2006/0184246 A1 | 8/2006 | Zwirkoski |
| 2006/0195165 A1 | 8/2006 | Gertner et al. |
| 2006/0217747 A1 | 9/2006 | Ferree |
| 2006/0229617 A1 | 10/2006 | Meller et al. |
| 2006/0229625 A1 | 10/2006 | Truckai et al. |
| 2006/0247787 A1 | 11/2006 | Rydell et al. |
| 2006/0253102 A1 | 11/2006 | Nance et al. |
| 2006/0253200 A1 | 11/2006 | Bao et al. |
| 2006/0258981 A1 | 11/2006 | Eidenschink |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0265077 A1 | 11/2006 | Zwirkoski |
| 2006/0271024 A1 | 11/2006 | Gertner et al. |
| 2006/0271061 A1 | 11/2006 | Beyar et al. |
| 2006/0276793 A1 | 12/2006 | Berry |
| 2006/0276819 A1 | 12/2006 | Osorio et al. |
| 2006/0282169 A1 | 12/2006 | Felt et al. |
| 2006/0287730 A1 | 12/2006 | Segal et al. |
| 2007/0027547 A1 | 2/2007 | Rydell et al. |
| 2007/0067032 A1 | 3/2007 | Felt et al. |
| 2007/0087031 A1 | 4/2007 | Ashman et al. |
| 2007/0100327 A1 | 5/2007 | Smith |
| 2007/0104416 A1 | 5/2007 | Shimizu et al. |
| 2007/0118143 A1 | 5/2007 | Ralph et al. |
| 2007/0123876 A1 | 5/2007 | Czartoski et al. |
| 2007/0123877 A1 | 5/2007 | Goldin et al. |
| 2007/0123878 A1 | 5/2007 | Shaver et al. |
| 2007/0161991 A1 | 7/2007 | Altarac et al. |
| 2007/0198023 A1 | 8/2007 | Sand et al. |
| 2007/0225705 A1 | 9/2007 | Osorio et al. |
| 2007/0233146 A1 | 10/2007 | Henniges et al. |
| 2007/0239148 A1 | 10/2007 | Scheller |
| 2007/0255287 A1 | 11/2007 | Rabiner |
| 2008/0015500 A1 | 1/2008 | Herweck et al. |
| 2008/0019657 A1 | 1/2008 | Maitland et al. |
| 2008/0021474 A1 | 1/2008 | Bonutti et al. |
| 2008/0039854 A1 | 2/2008 | Rabiner |
| 2008/0080205 A1 | 4/2008 | Forrester et al. |
| 2008/0103505 A1 | 5/2008 | Fransen |
| 2008/0125784 A1 | 5/2008 | Rabiner et al. |
| 2008/0154266 A1 | 6/2008 | Protopsaltis et al. |
| 2008/0154368 A1 | 6/2008 | Justis |
| 2008/0154373 A1 | 6/2008 | Protopsaltis et al. |
| 2008/0183122 A1 | 7/2008 | Fisher et al. |
| 2008/0188805 A1 | 8/2008 | Davies et al. |
| 2008/0188858 A1 | 8/2008 | Luzzi et al. |
| 2008/0234820 A1 | 9/2008 | Felt et al. |
| 2008/0249529 A1 | 10/2008 | Zarda et al. |
| 2008/0255560 A1 | 10/2008 | Myers et al. |
| 2008/0269750 A1 | 10/2008 | Justin |
| 2008/0287951 A1 | 11/2008 | Stoneburger et al. |
| 2008/0308753 A1 | 12/2008 | Stuba et al. |
| 2009/0005782 A1 | 1/2009 | Chirico et al. |
| 2009/0018524 A1 | 1/2009 | Greenhalgh et al. |
| 2009/0024166 A1 | 1/2009 | Carl et al. |
| 2009/0048629 A1 | 2/2009 | Rabiner |
| 2009/0054900 A1 | 2/2009 | Rabiner et al. |
| 2009/0076610 A1 | 3/2009 | Afzal et al. |
| 2009/0093887 A1 | 4/2009 | Walter et al. |
| 2009/0112196 A1 | 4/2009 | Rabiner et al. |
| 2009/0118833 A1 | 5/2009 | Hudgins et al. |
| 2009/0125028 A1 | 5/2009 | Teisen et al. |
| 2009/0171265 A1 | 7/2009 | Doty et al. |
| 2009/0171358 A1 | 7/2009 | Chang et al. |
| 2009/0177204 A1 | 7/2009 | Colleran et al. |
| 2009/0182336 A1 | 7/2009 | Brenzel et al. |
| 2009/0187192 A1 | 7/2009 | Rabiner et al. |
| 2009/0216232 A1 | 8/2009 | Buford, III et al. |
| 2009/0228007 A1 | 9/2009 | Justin et al. |
| 2009/0254064 A1 | 10/2009 | Boatman |
| 2009/0287309 A1 | 11/2009 | Walch et al. |
| 2009/0306589 A1 | 12/2009 | Tilson et al. |
| 2010/0076503 A1 | 3/2010 | Mordechay et al. |
| 2010/0234958 A1 | 9/2010 | Linares |
| 2010/0241178 A1 | 9/2010 | Tilson et al. |
| 2010/0249942 A1 | 9/2010 | Goswami et al. |
| 2010/0256641 A1 | 10/2010 | Rabiner et al. |
| 2010/0262069 A1 | 10/2010 | Rabiner et al. |
| 2010/0262188 A1 | 10/2010 | Rabiner et al. |
| 2010/0265733 A1 | 10/2010 | O'Leary et al. |
| 2010/0318087 A1 | 12/2010 | Scribner et al. |
| 2010/0331850 A1 | 12/2010 | Rabiner |
| 2011/0004213 A1 | 1/2011 | Rabiner et al. |
| 2011/0009871 A1 | 1/2011 | Rabiner |
| 2011/0029093 A1 | 2/2011 | Bojarski et al. |
| 2011/0046746 A1 | 2/2011 | Rabiner et al. |
| 2011/0077651 A1 | 3/2011 | Lozier et al. |

(56) References Cited

U.S. PATENT DOCUMENTS

| | | |
|---|---|---|
| 2011/0082504 A1 | 4/2011 | Singhatt et al. |
| 2011/0098713 A1 | 4/2011 | Rabiner et al. |
| 2011/0110114 A1 | 5/2011 | Papac et al. |
| 2011/0112588 A1 | 5/2011 | Linderman et al. |
| 2011/0118740 A1 | 5/2011 | Rabiner et al. |
| 2011/0137317 A1 | 6/2011 | O'Halloran et al. |
| 2011/0160870 A1 | 6/2011 | Baumgartner et al. |
| 2011/0166306 A1 | 7/2011 | Stansbury et al. |
| 2011/0218826 A1 | 9/2011 | Krinke et al. |
| 2011/0268866 A1 | 11/2011 | Parker |
| 2011/0288522 A1 | 11/2011 | Hollowel et al. |
| 2011/0313356 A1 | 12/2011 | Rabiner et al. |
| 2012/0016371 A1 | 1/2012 | O'Halloran et al. |
| 2012/0022540 A1 | 1/2012 | Chasmawala et al. |
| 2012/0029102 A1 | 2/2012 | Rose et al. |
| 2012/0041557 A1 | 2/2012 | Frigg |
| 2012/0065643 A1 | 3/2012 | Rabiner et al. |
| 2012/0165941 A1 | 6/2012 | Rabiner et al. |
| 2012/0259375 A1 | 10/2012 | Druma et al. |
| 2012/0262939 A1 | 10/2012 | O'Leary et al. |
| 2012/0289968 A1 | 11/2012 | Rabiner |
| 2012/0316652 A1 | 12/2012 | Renganath et al. |
| 2013/0003406 A1 | 1/2013 | O'Leary et al. |
| 2013/0006304 A1 | 1/2013 | Rabiner et al. |
| 2013/0012998 A1 | 1/2013 | Altarac et al. |
| 2013/0013008 A1 | 1/2013 | Rabiner et al. |
| 2013/0013009 A1 | 1/2013 | Colleran et al. |
| 2013/0013010 A1 | 1/2013 | Rabiner et al. |
| 2013/0018482 A1 | 1/2013 | Meridew et al. |
| 2013/0023876 A1 | 1/2013 | Rabiner et al. |
| 2013/0023877 A1 | 1/2013 | Rabiner et al. |
| 2013/0023886 A1 | 1/2013 | Rabiner et al. |
| 2013/0041472 A1 | 2/2013 | Rabiner et al. |
| 2013/0046390 A1 | 2/2013 | Rabiner et al. |
| 2013/0066326 A1 | 3/2013 | Rabiner et al. |
| 2013/0158607 A1 | 6/2013 | Rabiner et al. |
| 2013/0184715 A1 | 7/2013 | Rabiner et al. |
| 2013/0310875 A1 | 11/2013 | Rabiner et al. |
| 2014/0018806 A1 | 1/2014 | DiPoto et al. |
| 2014/0135847 A1 | 5/2014 | Rabiner et al. |
| 2014/0142581 A1 | 5/2014 | Rabiner et al. |
| 2014/0148813 A1 | 5/2014 | Rabiner et al. |
| 2014/0163453 A1 | 6/2014 | Rabiner et al. |
| 2014/0180288 A1 | 6/2014 | Rabiner et al. |
| 2015/0066028 A1 | 3/2015 | Rabiner et al. |
| 2015/0066085 A1 | 3/2015 | Rabiner et al. |
| 2015/0080900 A1 | 3/2015 | Rabiner et al. |
| 2015/0088268 A1 | 3/2015 | Rabiner et al. |
| 2015/0374498 A1 | 12/2015 | Rabiner et al. |
| 2016/0022333 A1 | 1/2016 | Rabiner et al. |
| 2016/0128750 A1 | 5/2016 | Rabiner et al. |
| 2016/0128836 A1 | 5/2016 | Rabiner et al. |
| 2017/0311996 A1 | 11/2017 | Rabiner et al. |
| 2018/0036054 A1 | 2/2018 | Rabiner et al. |
| 2018/0092672 A1 | 4/2018 | Rabiner et al. |
| 2019/0021773 A1 | 1/2019 | Rabiner et al. |
| 2019/0231533 A1 | 8/2019 | Rabiner et al. |

FOREIGN PATENT DOCUMENTS

| | | |
|---|---|---|
| EP | 2 298 201 | 3/2011 |
| JP | 2001-527437 | 12/2001 |
| JP | 2004-526525 | 9/2002 |
| JP | 2005-511143 | 4/2005 |
| JP | 2006-212425 | 8/2006 |
| NL | 9001858 | 3/1992 |
| WO | WO 1998/38918 | 9/1998 |
| WO | WO 1999/043266 | 9/1999 |
| WO | WO 2002/030338 | 4/2002 |
| WO | WO 2002/043628 | 6/2002 |
| WO | WO 2003/047472 | 6/2003 |
| WO | WO 2004/045393 | 6/2004 |
| WO | WO 2004/058045 | 7/2004 |
| WO | WO 2004/073563 | 9/2004 |
| WO | WO 2004/112661 | 12/2004 |
| WO | WO 2005/102224 | 11/2005 |
| WO | WO 2005/112804 | 12/2005 |
| WO | WO 2006/016807 | 2/2006 |
| WO | WO 2007/002251 | 1/2007 |
| WO | WO 2007/059259 | 5/2007 |
| WO | WO 2007/075375 | 7/2007 |
| WO | WO 2007/127255 | 11/2007 |
| WO | WO 2007/127260 | 11/2007 |
| WO | WO 2008/021972 | 2/2008 |
| WO | WO 2008/039811 | 4/2008 |
| WO | WO 2008/063265 | 5/2008 |
| WO | WO 2008/096363 | 8/2008 |
| WO | WO 2009/059090 | 5/2009 |
| WO | WO 2009/064847 | 5/2009 |
| WO | WO 2009/082688 | 7/2009 |
| WO | WO 2009/088927 | 7/2009 |
| WO | WO 2009/091811 | 7/2009 |
| WO | WO 2009/131999 | 10/2009 |
| WO | WO 2010/050965 | 5/2010 |
| WO | WO 2010/118158 | 10/2010 |
| WO | WO 2011/060062 | 5/2011 |
| WO | WO 2011/066522 | 6/2011 |
| WO | WO 2011/071567 | 6/2011 |
| WO | WO 2011/162910 | 12/2011 |
| WO | WO 2012/050583 | 4/2012 |
| WO | WO 2012/051312 | 4/2012 |
| WO | WO 2012/088432 | 6/2012 |
| WO | WO 2013/013069 | 1/2013 |
| WO | WO 2013/013071 | 1/2013 |
| WO | WO 2013/013072 | 1/2013 |
| WO | WO 2013/059609 | 4/2013 |
| WO | WO 2014/011669 | 1/2014 |
| WO | WO 2014/100427 | 6/2014 |

OTHER PUBLICATIONS

Maruyama et al., "Metacarpal Fracture Fixation with Absorbable Polyglycolide Rods and Stainless Steel K Wires: A Biomechanical Comparison", Journal of Biomedical Materials Research (Applied Biomaterials), vol. 33, Issue 1, pp. 9-12, Apr. 1996.

Waris et al., "Bioabsorbable Miniplating Versus Metallic Fixation for Metacarpal Fractures", Clinical Orthopaedics and Related Research, No. 410, pp. 310-319, May 2003.

Waris et al., "Self-Reinforced Bioabsorbable Versus Metallic Fixation Systems for Metacarpal and Phalangeal Fractures: A Biomechanical Study", The Journal of Hand Surgery, vol. 27A, No. 5, pp. 902-909, Sep. 2002.

PCT International Search Report based on PCT/US07/20402 dated Apr. 1, 2008.

PCT International Search Report based on PCT/US07/10050 dated Apr. 17, 2008.

PCT International Search Report based on PCT/US07/10038 dated Aug. 27, 2008.

PCT International Search Report based on PCT/US08/81929 dated Jan. 12, 2009.

PCT International Search Report based on PCT/US08/81924 dated Feb. 9, 2009.

PCT International Search Report based on PCT/US08/87630 dated Feb. 24, 2009.

USPTO Office Action in U.S. Appl. No. 11/789,906 dated Apr. 29, 2009.

USPTO Office Action in U.S. Appl. No. 11/789,906 dated Mar. 11, 2010.

USPTO Office Action in U.S. Appl. No. 11/789,906 dated Apr. 30, 2010.

USPTO Office Action in U.S. Appl. No. 11/789,907 dated May 11, 2010.

USPTO Office Action in U.S. Appl. No. 11/903,123 dated Jul. 1, 2010.

PCT International Search Report based on PCT/US10/30275 dated Aug. 11, 2010.

USPTO Office Action in U.S. Appl. No. 12/262,411 dated Sep. 1, 2010.

USPTO Office Action in U.S. Appl. No. 11/964,370 dated Dec. 9, 2010.

(56) References Cited

OTHER PUBLICATIONS

PCT International Search Report based on PCT/US10/56219 dated Jan. 20, 2011.
PCT International Search Report based on PCT/US10/46003 dated May 24, 2011.
PCT International Search Report based on PCT/US11/38389 dated Sep. 22, 2011.
USPTO Office Action in U.S. Appl. No. 11/964,370 dated Apr. 28, 2011.
USPTO Office Action in U.S. Appl. No. 11/964,370 dated Sep. 23, 2011.
USPTO Office Action in U.S. Appl. No. 12/858,924 dated Oct. 24, 2011.
USPTO Office Action in U.S. Appl. No. 12/755,784 dated Dec. 23, 2011.
USPTO Office Action in U.S. Appl. No. 12/886,288 dated Dec. 27, 2011.
USPTO Office Action in U.S. Appl. No. 12/875,460 dated Mar. 8, 2012.
USPTO Office Action in U.S. Appl. No. 11/964,370 dated Mar. 16, 2012.
USPTO Office Action in U.S. Appl. No. 12/858,924 dated Apr. 4, 2012.
PCT International Search Report based on PCT/US11/66871 dated May 1, 2012.
USPTO Office Action in U.S. Appl. No. 12/756,014 dated May 11, 2012.
USPTO Office Action in U.S. Appl. No. 12/262,370 dated May 29, 2012.
USPTO Office Action in U.S. Appl. No. 12/943,544 dated Jun. 8, 2012.
USPTO Office Action in U.S. Appl. No. 12/886,288 dated Jun. 26, 2012.
USPTO Office Action in U.S. Appl. No. 11/964,370 dated Jul. 6, 2012.
Extended European Search Report based on EP 07 75 6022 dated Jul. 19, 2012.
Extended European Search Report based on EP 07 75 6016 dated Jul. 18, 2012.
USPTO Office Action in U.S. Appl. No. 12/755,784 dated Aug. 1, 2012.
USPTO Office Action in U.S. Appl. No. 12/858,924 dated Aug. 2, 2012.
USPTO Office Action in U.S. Appl. No. 12/886,288 dated Aug. 15, 2012.
PCT International Search Report based on PCT/US12/47447 dated Oct. 2, 2012.
PCT International Search Report based on PCT/US12/47446 dated Oct. 15, 2012.
PCT International Search Report based on PCT/US12/47444 dated Oct. 18, 2012.
USPTO Office Action in U.S. Appl. No. 12/756,014 dated Oct. 25, 2012.
USPTO Office Action in U.S. Appl. No. 12/859,680 dated Nov. 9, 2012.
USPTO Office Action in U.S. Appl. No. 12/943,544 dated Dec. 3, 2012.
USPTO Office Action in U.S. Appl. No. 12/262,370 dated Dec. 14, 2012.
International Search Report and Written Opinion for PCT/US2012/061047 dated Jan. 7, 2013.
USPTO Office Action in U.S. Appl. No. 12/859,680 dated Jan. 17, 2013.
USPTO Office Action in U.S. Appl. No. 12/756,014 dated Jan. 22, 2013.
USPTO Office Action in U.S. Appl. No. 13/088,916 dated Jan. 23, 2013.
USPTO Office Action in U.S. Appl. No. 13/617,557 dated Feb. 4, 2013.
USPTO Office Action in U.S. Appl. No. 12/755,784 dated Mar. 13, 2013.
USPTO Office Action in U.S. Appl. No. 13/616,416 dated Mar. 25, 2013.
USPTO Office Action in U.S. Appl. No. 13/561,249 dated Apr. 23, 2013.
USPTO Office Action in U.S. Appl. No. 12/262,370 dated Apr. 26, 2013.
USPTO Office Action in U.S. Appl. No. 13/088,916 dated May 13, 2013.
Supplemental European Search Report based on EP 08 87 7881 dated May 15, 2013.
USPTO Office Action in U.S. Appl. No. 13/772,947 dated Jun. 19, 2013.
USPTO Office Action in U.S. Appl. No. 12/859,680 dated Jul. 9, 2013.
USPTO Office Action in U.S. Appl. No. 13/561,249 dated Sep. 16, 2013.
USPTO Office Action in U.S. Appl. No. 13/088,916 dated Sep. 17, 2013.
USPTO Office Action in U.S. Appl. No. 12/943,544 dated Sep. 25, 2013.
PCT International Search Report based on PCT/US13/049773 dated Oct. 1, 2013.
USPTO Office Action in U.S. Appl. No. 13/617,557 dated Oct. 9, 2013.
Extended European Search Report based on EP 10 76 2390 dated Oct. 30, 2013.
USPTO Office Action in U.S. Appl. No. 12/262,370 dated Nov. 21, 2013.
USPTO Office Action in U.S. Appl. No. 12/983,496 dated Feb. 5, 2014.
USPTO Office Action in U.S. Appl. No. 12/756,014 dated Feb. 13, 2014.
USPTO Office Action in U.S. Appl. No. 13/617,181 dated Feb. 25, 2014.
PCT International Search Report based on PCT/US13/076598 dated Mar. 19, 2014.
USPTO Office Action in U.S. Appl. No. 13/655,808 dated Mar. 27, 2014.
USPTO Office Action in U.S. Appl. No. 13/553,247 dated May 7, 2014.
Extended European Search Report based on EP 14156473 dated May 13, 2014.
USPTO Office Action in U.S. Appl. No. 13/800,518 dated Jun. 10, 2014.
USPTO Office Action in U.S. Appl. No. 12/262,370 dated Jun. 26, 2014.
USPTO Office Action in U.S. Appl. No. 13/617,557 dated Jun. 27, 2014.
USPTO Office Action in U.S. Appl. No. 13/335,110 dated Jul. 31, 2014.
USPTO Office Action in U.S. Appl. No. 13/616,781 dated Aug. 26, 2014.
USPTO Office Action in U.S. Appl. No. 13/730,521 dated Sep. 8, 2014.
USPTO Office Action in U.S. Appl. No. 12/756,014 dated Oct. 7, 2014.
USPTO Office Action in U.S. Appl. No. 13/553,450 dated Oct. 24, 2014.
USPTO Office Action in U.S. Appl. No. 13/335,110 dated Oct. 24, 2014.
USPTO Office Action in U.S. Appl. No. 13/553,247 dated Dec. 5, 2014.
USPTO Office Action in U.S. Appl. No. 13/553,051 dated Dec. 23, 2014.
USPTO Office Action in U.S. Appl. No. 12/262,370 dated Jan. 14, 2015.
USPTO Office Action in U.S. Appl. No. 13/617,557 dated Jan. 15, 2015.
USPTO Office Action in U.S. Appl. No. 13/335,110 dated Feb. 9, 2015.

(56) References Cited

OTHER PUBLICATIONS

USPTO Office Action in U.S. Appl. No. 13/796,085 dated Feb. 12, 2015.
USPTO Office Action in U.S. Appl. No. 13/553,051 dated Mar. 31, 2015.
USPTO Office Action in U.S. Appl. No. 13/553,247 dated May 1, 2015.
USPTO Office Action in U.S. Appl. No. 13/297,097 dated May 29, 2015.
USPTO Office Action in U.S. Appl. No. 14/171,036 dated Jun. 1, 2015.
USPTO Office Action in U.S. Appl. No. 14/164,846 dated Jun. 4, 2015.
USPTO Office Action in U.S. Appl. No. 13/617,557 dated Jul. 15, 2015.
USPTO Office Action in U.S. Appl. No. 13/796,085 dated Jul. 17, 2015.
USPTO Office Action in U.S. Appl. No. 13/553,051 dated Sep. 11, 2015.
USPTO Office Action in U.S. Appl. No. 13/553,247 dated Sep. 23, 2015.
USPTO Office Action in U.S. Appl. No. 14/164,846 dated Oct. 14, 2015.
USPTO Office Action in U.S. Appl. No. 14/171,036 dated Oct. 15, 2015.
USPTO Office Action in U.S. Appl. No. 12/262,370 dated Oct. 22, 2015.
USPTO Office Action in U.S. Appl. No. 13/796,085 dated Nov. 27, 2015.
USPTO Office Action in U.S. Appl. No. 13/553,051 dated Jan. 6, 2016.
USPTO Office Action in U.S. Appl. No. 13/617,557 dated Jan. 14, 2016.
USPTO Office Action in U.S. Appl. No. 14/177,748 dated Jan. 25, 2016.
USPTO Office Action in U.S. Appl. No. 14/535,913 dated Feb. 22, 2016.
USPTO Office Action in U.S. Appl. No. 13/553,247 dated Mar. 2, 2016.
USPTO Office Action in U.S. Appl. No. 14/535,971 dated Mar. 4, 2016.
USPTO Office Action in U.S. Appl. No. 12/262,370 dated Jun. 2, 2016.
USPTO Office Action in U.S. Appl. No. 13/796,085 dated Jul. 1, 2016.
USPTO Office Action in U.S. Appl. No. 14/535,913 dated Sep. 26, 2016.
USPTO Office Action in U.S. Appl. No. 13/553,247 dated Oct. 13, 2016.
USPTO Office Action in U.S. Appl. No. 13/996,275 dated Nov. 14, 2016.
PCT International Search Report based on PCT/US2016/60603 dated Jan. 30, 2017.
USPTO Office Action in U.S. Appl. No. 14/874,946 dated May 17, 2017.
USPTO Office Action in U.S. Appl. No. 14/988,058 dated Jun. 12, 2017.
USPTO Office Action in U.S. Appl. No. 15/834,459 dated Mar. 30, 2018.
USPTO Office Action in U.S. Appl. No. 14/843,286 dated Jun. 7, 2018.
USPTO Office Action in U.S. Appl. No. 15/652,147 dated Jan. 17, 2019.
USPTO Office Action in U.S. Appl. No. 15/655,326 dated Jan. 30, 2019.
USPTO Office Action in U.S. Appl. No. 15/652,147 dated Jul. 30, 2018.
USPTO Office Action in U.S. Appl. No. 15/655,326 dated Aug. 7, 2018.
USPTO Office Action in U.S. Appl. No. 15/652,147 dated Jun. 24, 2019.

* cited by examiner

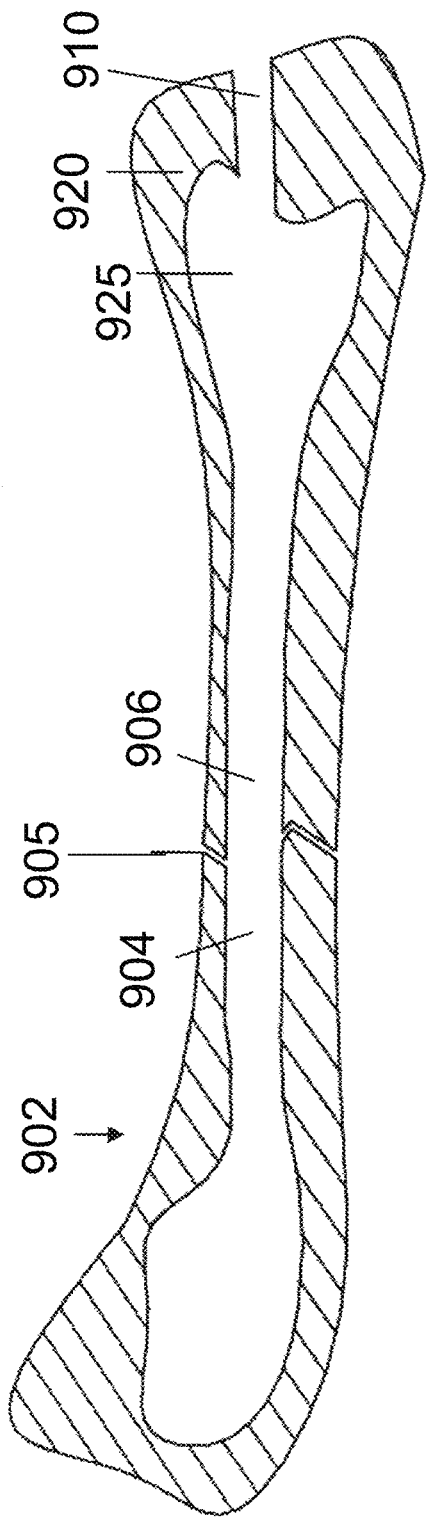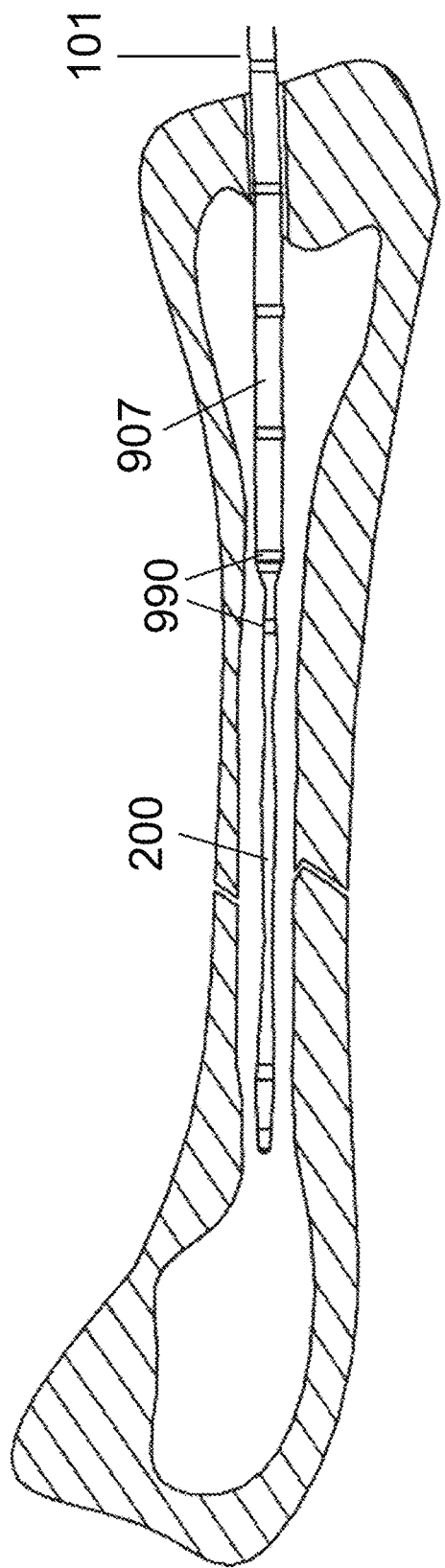
FIG. 9A
FIG. 9B

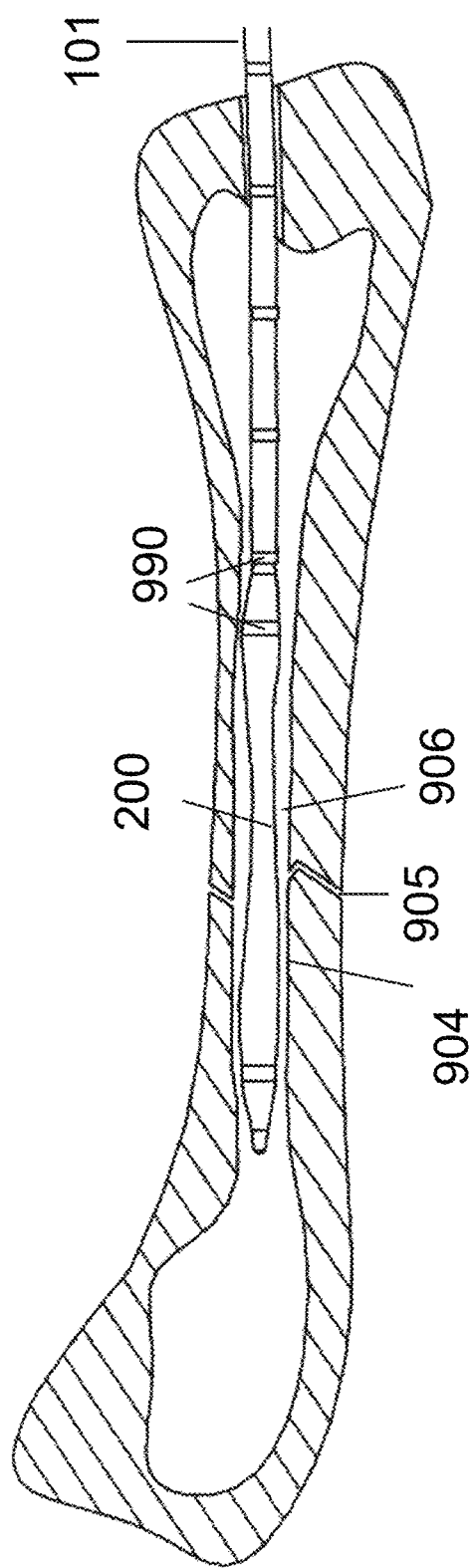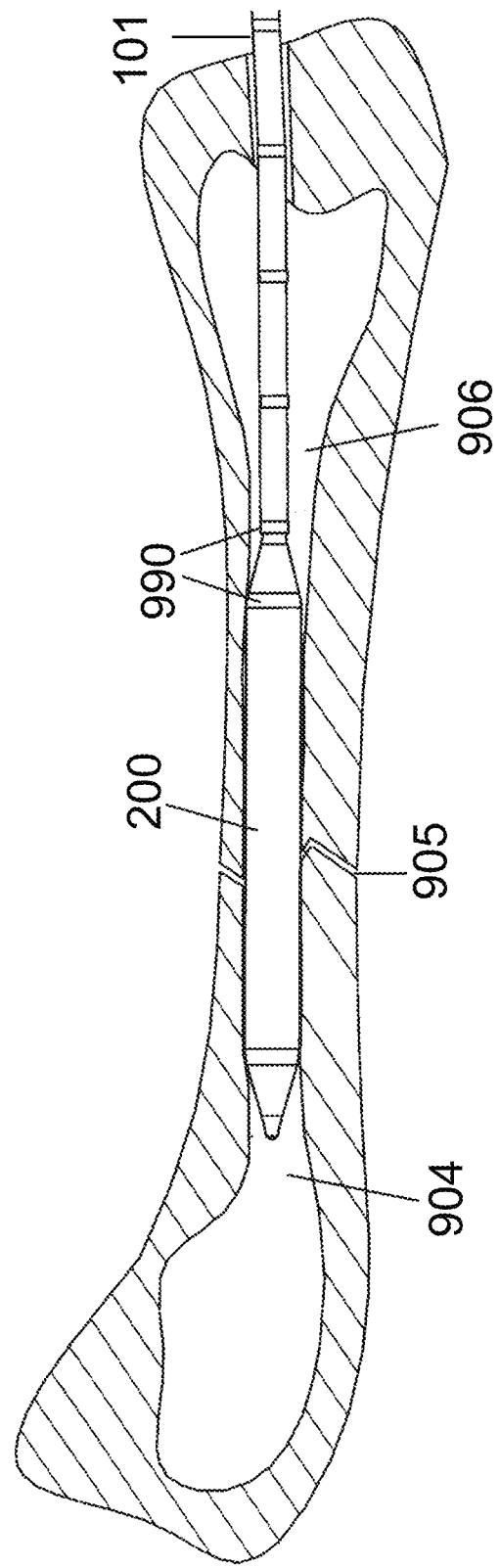

DISTAL TIP FOR BONE FIXATION DEVICES

RELATED APPLICATIONS

This application is a continuation patent application of U.S. patent application Ser. No. 13/796,085, filed Mar. 12, 2013 which claims the benefit of and priority to U.S. Provisional Application No. 61/739,972, filed on Dec. 20, 2012, each of which is incorporated herein by reference in their entireties.

FIELD

The embodiments disclosed herein relate to distal tip for systems for use during an bone fixation procedure and methods of their use.

BACKGROUND

Fracture repair is the process of rejoining and realigning the ends of broken bones. Currently there are several internal approaches to repair, strengthen and support a fractured bone. Conventional internal fixation devices include wires, plates, rods, pins, nails, and screws to support the fractured bone directly, as well as the addition of reinforcing materials to the fractured bone. Newer internal fixation devices include expandable members that can be expanded with curable material and hardened inside the intramedullary cavity of a bone to provide a conformal fit inside the intramedullary cavity, which leads to greater support and strength to the healing bone. However, there is still a need for further improvements of such internal fixation devices.

SUMMARY

Distal tip designs for bone fixation devices are disclosed. According to some aspects illustrated herein, there is provided a device for bone fixation that includes a delivery catheter comprising an outer tube and an inner tube disposed within the outer tube and extending beyond the outer tube; an expandable member having a proximal region and a distal region, the expandable member being releasably attached about a distal end of the delivery catheter at the proximal region of the expandable member, and a distal cap attached to the distal region of the expandable member to seal the expandable member; and an inner compartment in the distal region of the expandable member, the inner tube and enable movement of the inner tube within the inner compartment.

According to some aspects illustrated herein, there is provided a system for bone fixation that includes a delivery catheter having a proximal end and a distal end; an expandable member having a proximal region and a distal region, wherein the expandable member is releasably attached about the distal end of the delivery catheter at the proximal region of the expandable member; a distal cap attached to the distal region of the expandable member to seal the expandable member; a light conducting fiber; and a light-sensitive liquid; wherein the delivery catheter has an inner void for passage of a light-sensitive liquid into the expandable member to expand the expandable member and an inner lumen for passage of the light conducting fiber into the expandable member to cure the light-sensitive liquid inside the expandable member.

According to some aspects illustrated herein, there is provided a method for bone fixation that includes advancing to a fractured bone a device comprising a delivery catheter having a proximal end and a distal end; an expandable member having a proximal region and a distal region, wherein the expandable member is attached about the distal end of the delivery catheter at the proximal region of the expandable member; and a distal cap attached to the distal region of the expandable member to seal the expandable member; positioning the expandable member within an intramedullary cavity of the fractured bone; expanding the expandable member with a light-sensitive liquid; and curing the light-sensitive liquid within the expandable member.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 9A, FIG. 9B, FIG. 9C, FIG. 9D and FIG. 9E illustrate an embodiment method for repairing a weakened or fractured bone of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Systems and methods for bone fixation procedures are disclosed herein. In some embodiments, distal tip designs for internal bone fixation devices are disclosed.

Figure 1:
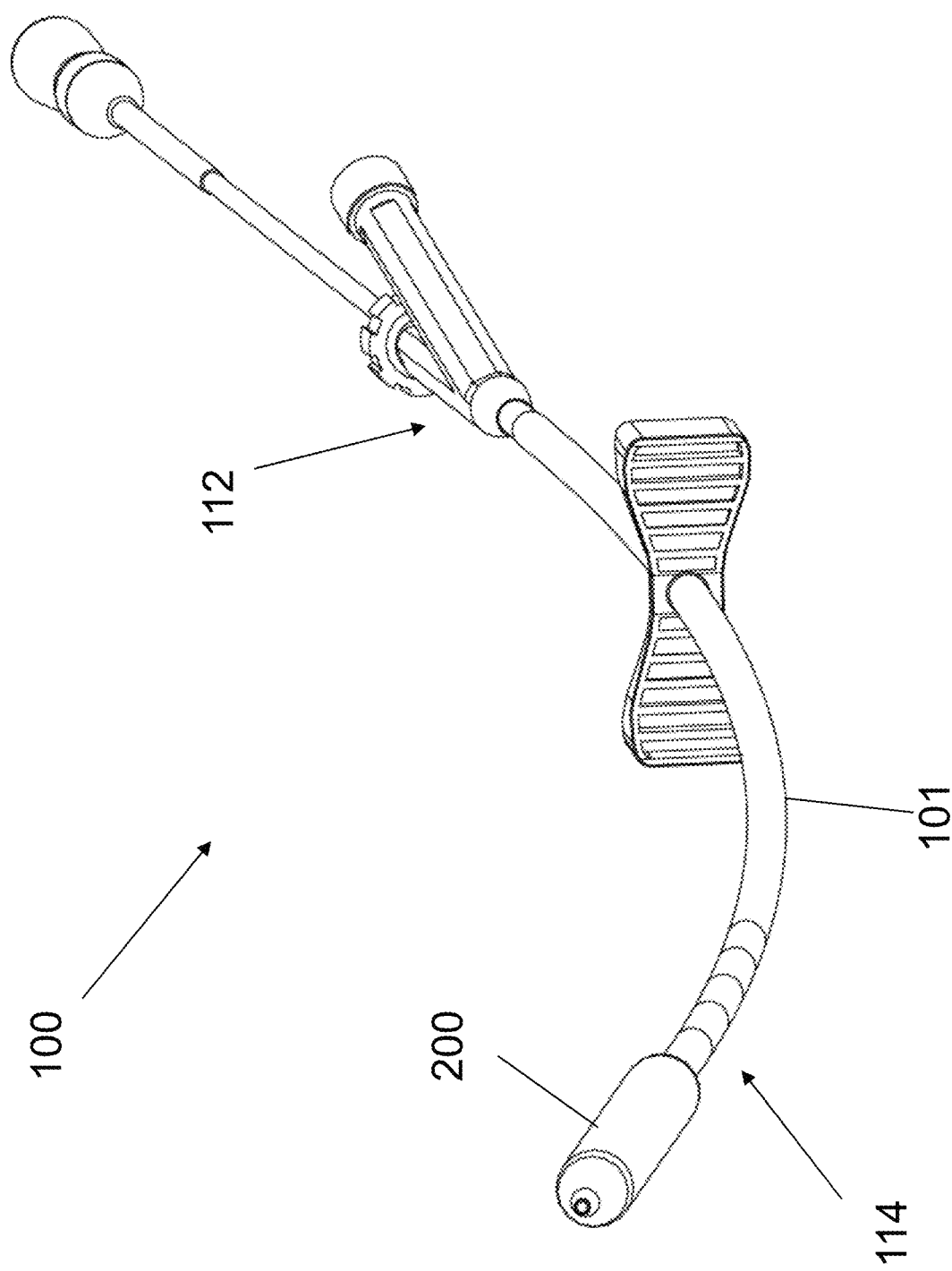
FIG. 1 is a prospective view of an embodiment of a device for repairing a weakened or fractured bone of the present disclosure.

FIG. 1 illustrates the main components of an embodiment of a device for repairing a weakened or fractured bone. The device 100 includes a delivery catheter 101 having an elongated shaft with a proximal end 112, a distal end 114, and a longitudinal axis therebetween. In an embodiment, the delivery catheter 101 has a diameter of about 3 mm. The distal end 104 of the delivery catheter 101 terminates in an expandable member 200 (also referred to herein as a conformable member or a balloon portion). The expandable member 200 may move from a deflated state to an inflated state when at least one reinforcing material is delivered to the expandable member 200. In some embodiments, the expandable member 200 may be releaseably attached to the delivery catheter 101. In some embodiments, the expandable member 200 may be placed inside an intramedullary cavity of a bone for internal bone fixation.

Figure 2:
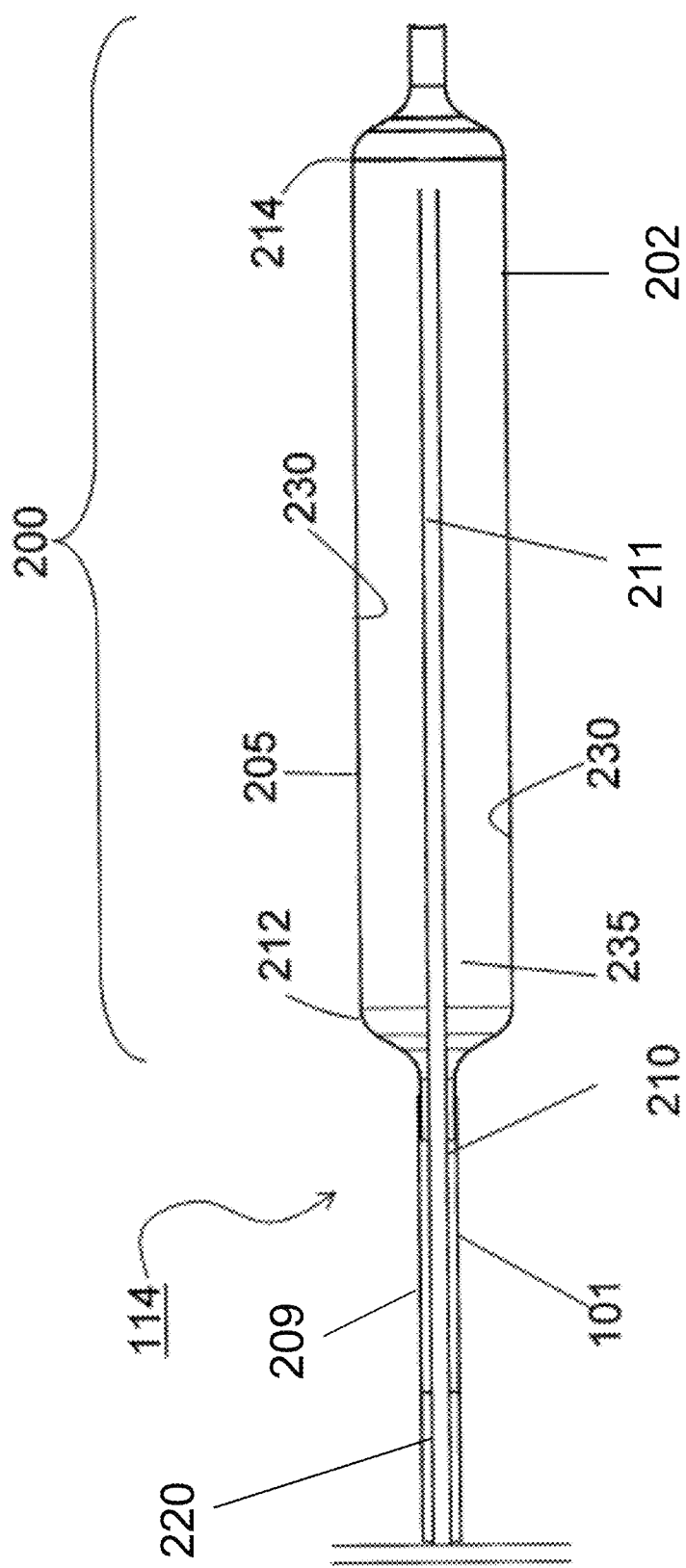
FIG. 2 is a close-up view of an embodiment of a distal end of a device for repairing a weakened or fractured bone of the present disclosure.

FIG. 2 is a side view of an embodiment of a distal end 114 of the flexible delivery catheter 101. The distal end 114 includes the expandable member 200 releasably mounted on the flexible delivery catheter 101. The expandable member 200 has a wall 202 with an outer surface 205 and an inner surface 230. The inner surface 230 defines an inner cavity 235. In some embodiments, the delivery catheter 101 may include multiple inner lumens or voids. For example, as shown in FIG. 2, the delivery catheter 101 may include an outer tube 209 and a central tube 220 concentrically disposed within the delivery catheter 101. An inner void 210 may be formed between the outer tube 209 and the central tube 220. The inner void 210 may be utilized for passing a light-sensitive liquid into the inner cavity 235 of the expandable member 200. In some embodiments, the central tube 220 includes an inner lumen 211 for passing a light-conducting fiber (which is not illustrated in FIG. 2) into the expandable member 200 to cure the light sensitive liquid inside the inner cavity 235 of the expandable member, as described in detail below. It should be noted that while the delivery catheter 101 is described as having the central lumen 220 concentric with the outer tube 209, the central lumen 220 may be off-set relative to the outer tube 209.

In some embodiments, the expandable member 200 is manufactured from a thin-walled, non-compliant (non-stretch/non-expansion) conformable material. The expandable member 200 may be formed of a pliable, resilient, conformable, and strong material, including but not limited to urethane, polyethylene terephthalate (PET), nylon elastomer and other similar polymers. In some embodiments, the expandable member 200 of the present disclosure is constructed out of a PET nylon aramid or other non-consumable materials. The expandable member 200 may be impregnated with a radiopaque material to enhance the visibility of the expandable member 200. The expandable member 200 is biocompatible, thus preventing or reducing possible adverse reactions after insertion into a fractured bone. In some embodiments, the expandable member 200 is made from a material that is non-toxic, non-antigenic and non-immunogenic.

The expandable member 200 includes a proximal area 212 and a distal area 214. The proximal area 212 of the expandable member 200 is releasably connected to the delivery catheter 101. The distal area 214 may be connected to the delivery catheter 101 in a variety of ways.

Figure 3:
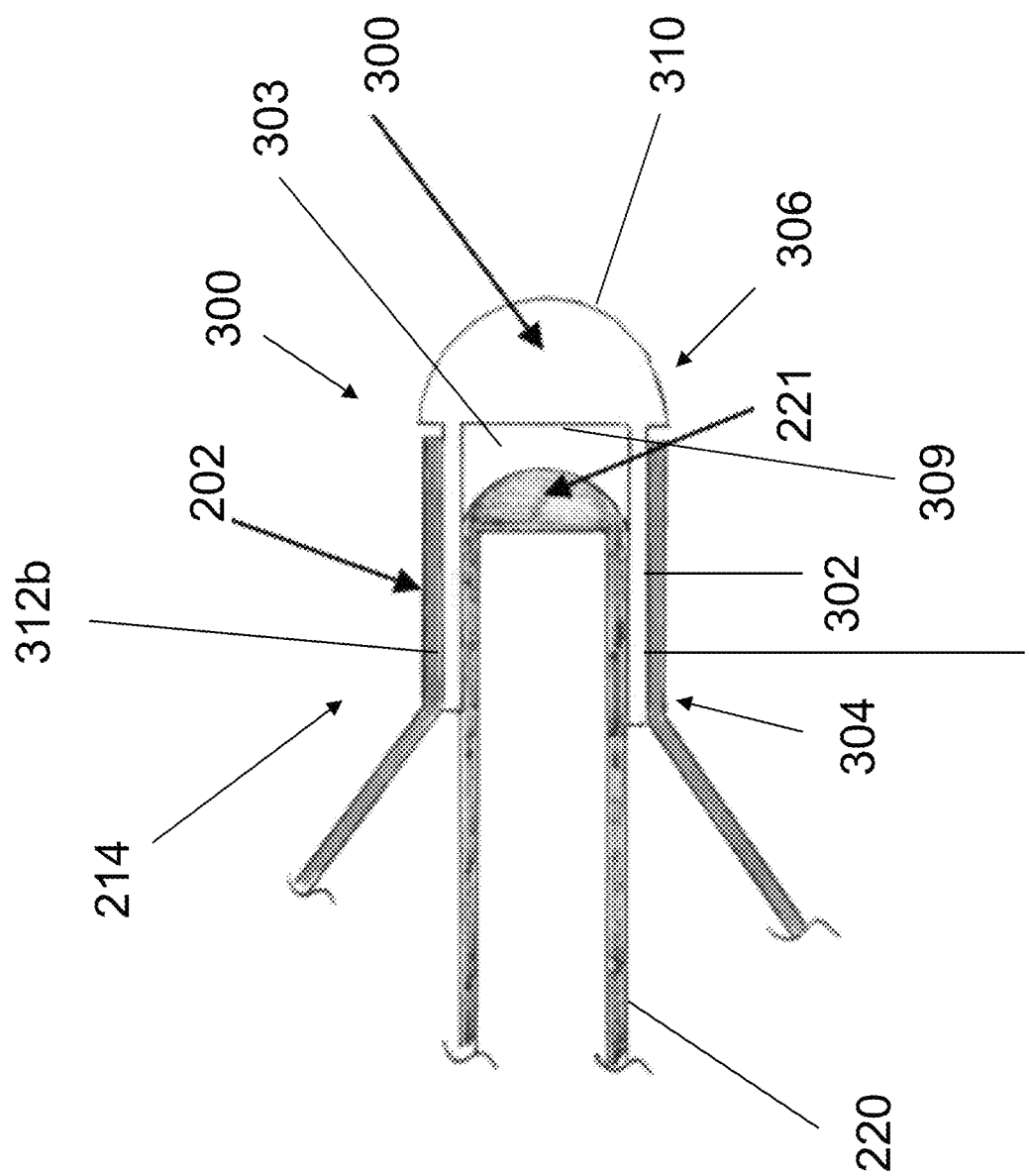
FIG. 3 illustrates an embodiment of a distal tip design for a device for repairing a weakened or fractured bone of the present disclosure.

In reference to FIG. 3, in some embodiments, the distal area 214 of the expandable member 200 may be connected to a distal cap 300, which may be disposed at the distal end of the central tube 220. The distal cap 300 terminates and seals off the area 214 of the expandable member 200 to prevent the flow of a light-sensitive liquid outside the balloon and the ingress of bodily fluids inside the balloon. One potential benefit of utilizing the distal cap 300 is ease of manufacture and more consistent tip quality when compared to traditional melt forming of expandable member 200 directly to the delivery catheter. An additional benefit of the use of the distal cap 300 may also include the ability to reflect back or scatter light radiating from the end of the conducting fiber to improve the light-sensitive liquid cure times or depth of cure. The reflected light from the distal cap 300 may increase the energy that is directed towards the light-sensitive liquid in the expandable member 200 and thus may increase the photo-initiation rate (and thus polymerization rate) of the light-sensitive liquid.

In some embodiments, the distal cap 300 may be formed, molded or machined from an implant grade polymer (e.g., PET), or another biocompatible material. The distal cap 300 may also be made from a filled material. For example, the PET polymer may be blended with a radiopaque material (e.g., barium sulfate, tungsten, tantalum, etc.) such that the distal cap 300 may be viewed with the assistance of fluoroscopic imaging. In some embodiments, the distal cap 300 may also be covered with a reflective material such as a gold film (or other metallic highly polished implant grade film) to enable the distal cap 300 to reflect light radiating from the end of the light pipe back into the balloon. This reflected light can help to reduce the cure time of the light sensitive liquid contained within the expandable member 200 to due to the increase in light energy directed at the light sensitive liquid. In some embodiments, the distal cap 300 may also be fabricated from a crystalline material (such as crystalline PET) to block the transmission of light through the end of the device 100 and to reflect and/or scatter the light back to the light sensitive liquid in the expandable member 200.

As illustrated in FIG. 3, a distal cap 300 includes a body 302 having a proximal end 304 and a distal end 306. The body 302 defines an inner compartment 303 for receiving the central tube 220 therein. In some embodiments, the inner compartment 303 is tubular to accommodate the central tube 220 therein. The proximal end 304 of the body 302 is open to allow the central tube 220 to be inserted into the inner compartment 303. The distal cap 300 may stabilize the central tube 220 and may minimize snaking or bowing of the central tube 220 during the operation. In some embodiments, the central tube 300 may be free floating within the distal cap 300, that is, the distal end of the central tube 220 is capable of movement within the inner compartment 303. In some embodiments, being free floating within the inner compartment 303, the central tube 220 can move within the inner compartment 303 in a radial direction, a longitudinal direction or both a radial direction and a longitudinal direction. Because in some embodiments the central tube 220 is free-floating, unrestrained or unbound within the inner compartment 303, the central tube 220 can automatically adjust to the pressure maintained within the expandable member 200 to minimize or even eliminate the deformation of the central tube along its length. For example, as the expandable member 200 expands and contracts in diameter and length during infusion or withdrawal of the light sensitive liquid, the central tube 220 can adjust in length thereby reducing the stress on the central tube 220 and the light conducting fiber inside the central tube 220. In some embodiments, where the central tube 220 is free floating within the distal cap 300, the pleating and wrapping of the expandable member 200 may be improved, which may prevent damage to the expandable member 200 during manufacturing (improved yields), decrease the likelihood of leak occurrence either during manufacturing or in use, and potentially result in improvement on profile (able to wrap down to a smaller diameter) and insertion force (due to reduced friction).

While the central tube 220 may be free floating, in some embodiments, the central tube 220 may also be tethered to the distal cap by means of a filament or fiber to prevent the central tube 220 from becoming completely dislodged from within the distal cap 300. The filament or fiber may be elastic or rigid under tension and compression. In some embodiments, the central tube 220 may be rigidly secured to the distal cap 300. The central tube 220 may be secured inside the compartment 303 by press fitting the central tube 220 into the compartment 303; applying permanent adhesive on the surfaces between the central tube 220 and the compartment 303; melt bonding the two surfaces together or other techniques.

The distal end 306 of the body 302 may be either open or closed. In some embodiments, the distal cap 300 closes the distal tip 306 of the body 302 to close the distal tip 306. The distal cap 300 includes an inner surface 309, which faces the body 302, and an outer surface 310, which faces away from the body 302. In some embodiments, the outer surface 310 of the distal cap 300 may be rounded or smooth to provide the device 100 with an atraumatic distal point. In some embodiments, the distal cap 300 may have a semi-circular shape with a flat inner surface and a curved outer surface. In some embodiments, the body 302 may be open as long as there is a seal created, such as by for example, sealing the central tube 220 to the inner surface of the inner compartment 303 to prevent movement of fluids in and out of the expandable member 200.

In reference to FIG. 3, in some embodiments, the material forming the expandable member 200 may be attached to the outer surface of the body 302. In some embodiments, the outer surface of the body 302 includes recessed attachment sections 312a, 312b to which the material of the expandable member 200 can be attached. In some embodiments, the outer surface of the body 302 may be recessed by a depth approximately equal to the thickness of the expandable member material. In this manner, when the expandable member material is attached to the body 302, the outside of the expandable member material is substantially aligned with the outer surface 310 of the distal cap 300. The material of the expandable member 200 can be attached to the body 302 by a variety of methods, including, without limitation, adhesives such as cyano-acrylates or epoxies, crimping metallic rings over the expandable potion, melt bonding the expandable member to the body 302 with the use of heat (e.g., RF generated), ultrasonically welding the expandable member to the body 302, or another method or combination of methods.

Figure 4:
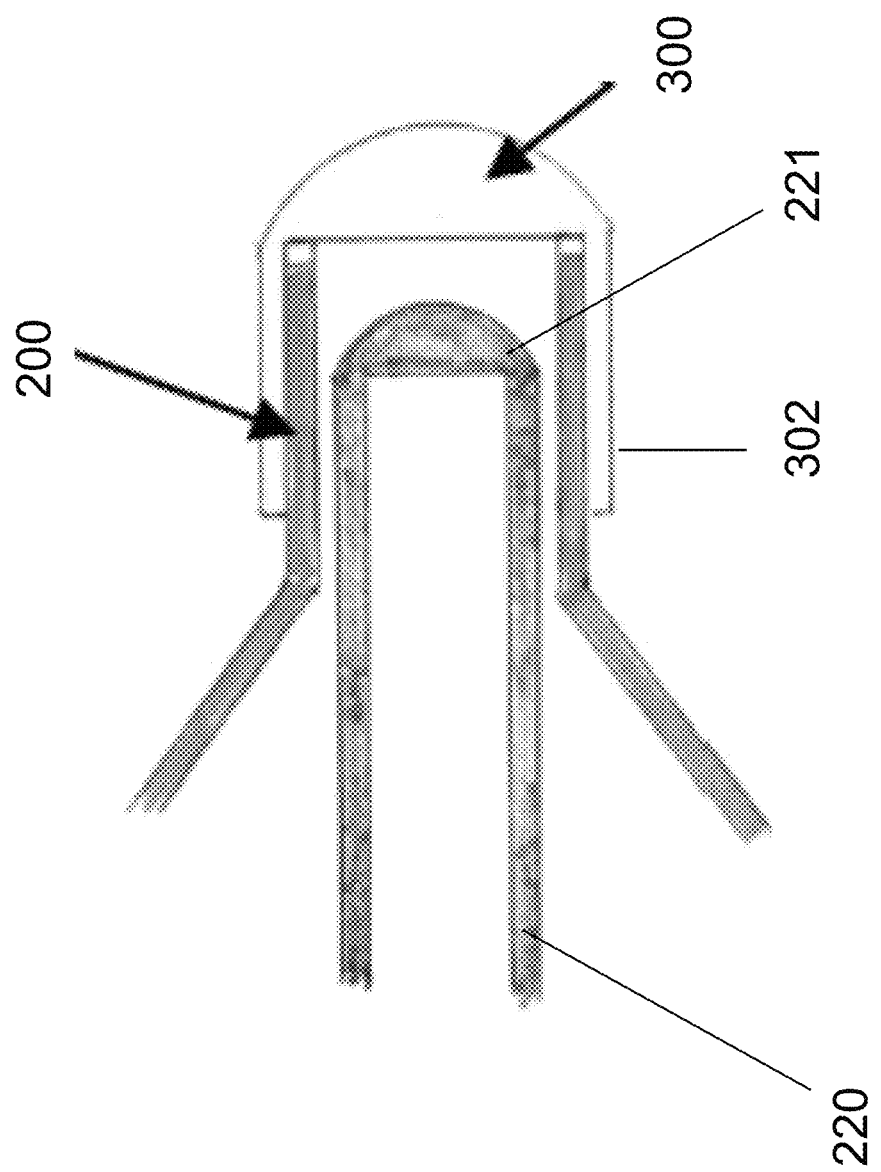
FIG. 4 illustrates an embodiment of a distal tip design for a device for repairing a weakened or fractured bone of the present disclosure.

In reference to FIG. 4, in some embodiments, the material of the expandable member 200 may be attached to the inner surface of the body 302 of the distal cap 300.

Figure 5:
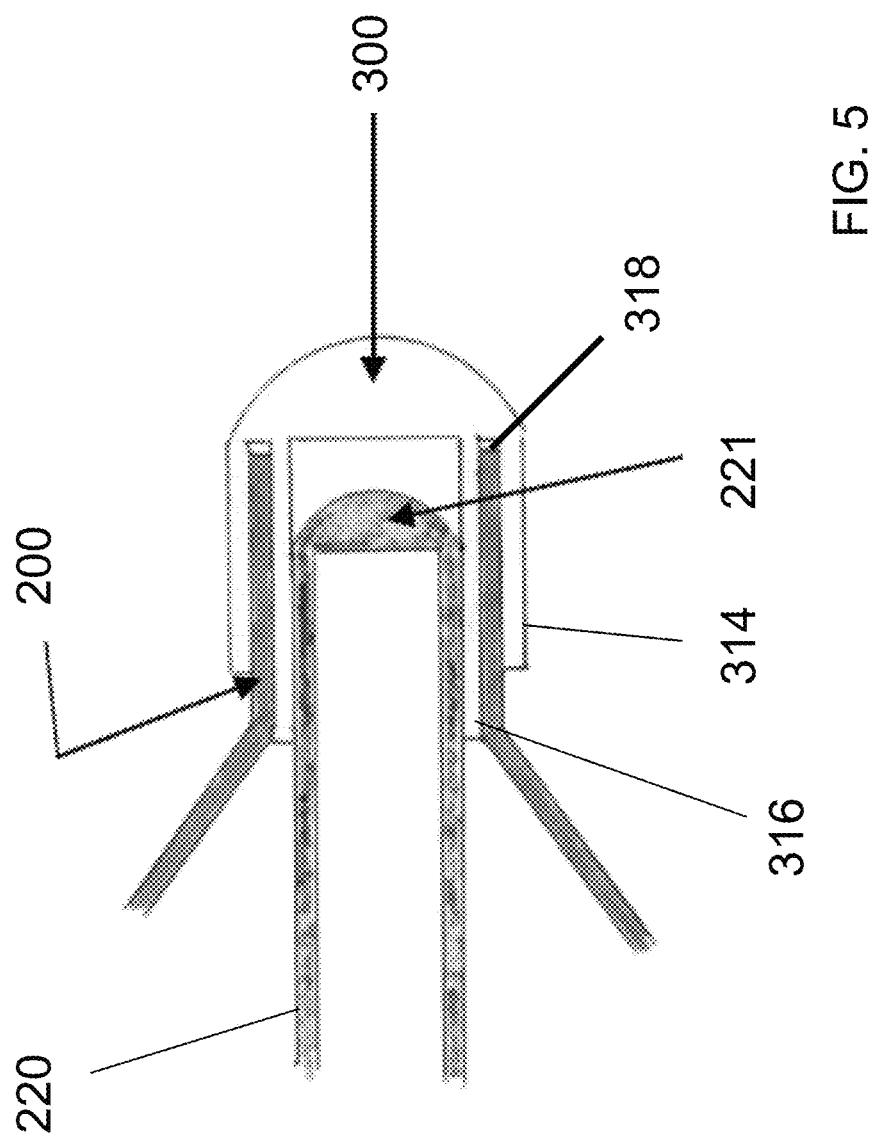
FIG. 5 illustrates an embodiment of a distal tip design for a device for repairing a weakened or fractured bone of the present disclosure.

In reference to FIG. 5, in some embodiments, the body 302 may have a slotted wall, formed by a first wall or prong 314 and a second wall or prong 316 spaced apart from one another to form a slot 318 between the first wall 314 and the second wall 316. The material of the expandable member 200 can be inserted into the slot 318 and secured within the slot 318 between the first wall 314 and the second wall 316 by a variety of methods. This design may provide additional separation resistance between the two components which may translate to an increase in burst pressure and fatigue resistance at this interface.

Figure 6:
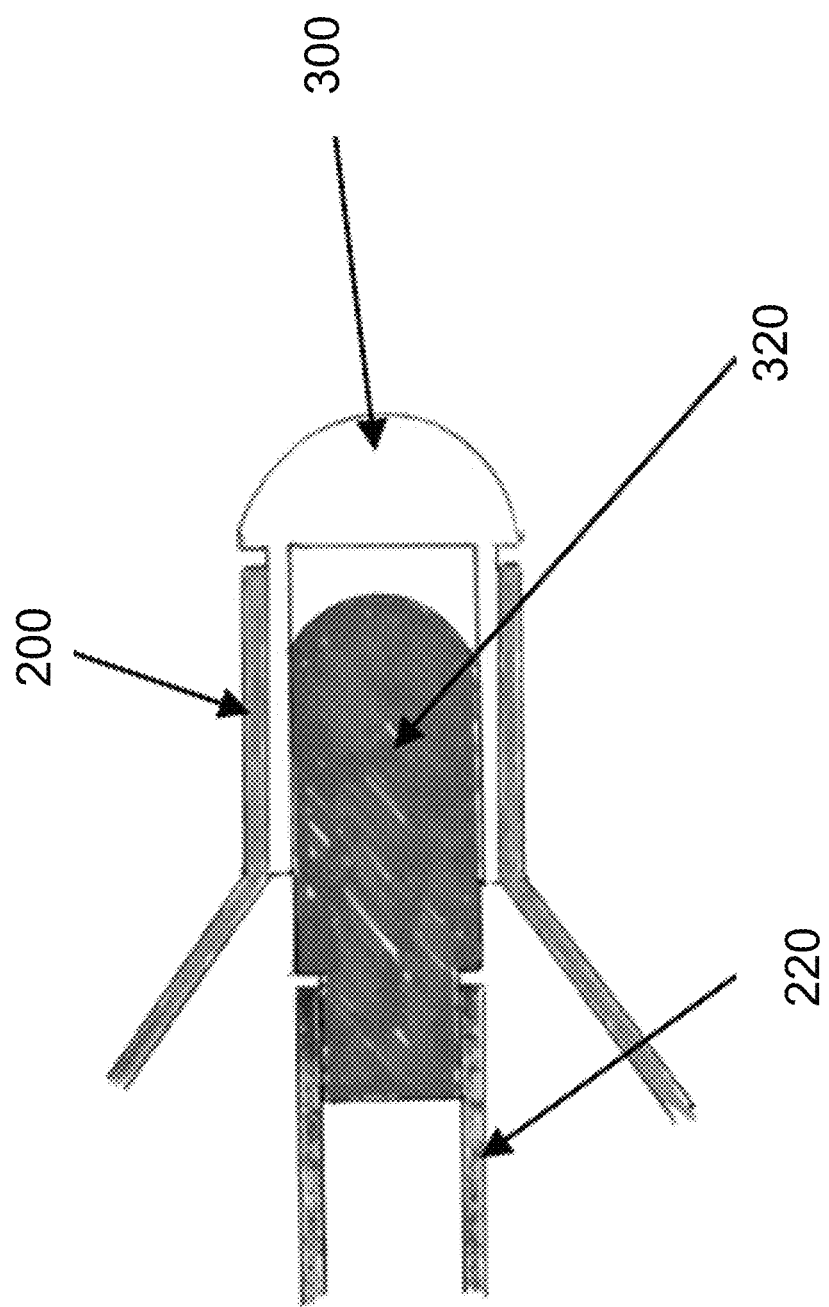
FIG. 6 illustrates an embodiment of a distal tip design for a device for repairing a weakened or fractured bone of the present disclosure.

In some embodiments, the central tube 220 may be sealed distally by a melt 221 formed by a process such as an RF heated mold (as shown in FIG. 3, FIG. 4 and FIG. 5). Alternatively, as shown in FIG. 6, the central tube 220 may be sealed with a tube plug 320 before being inserted into the distal cap 300. The tube plug 320 can be fabricated in a similar fashion to the distal cap 300 in terms of material and fillers (providing the same benefits described previously for the distal cap 300). Alternatively, the tip of the central tube 220 can be left not sealed, as long as there is a seal between the outer surface of the central tube 220 and the inner surface of the compartment 303 to prevent leaks into or out of the central tube 220.

Figure 7B:
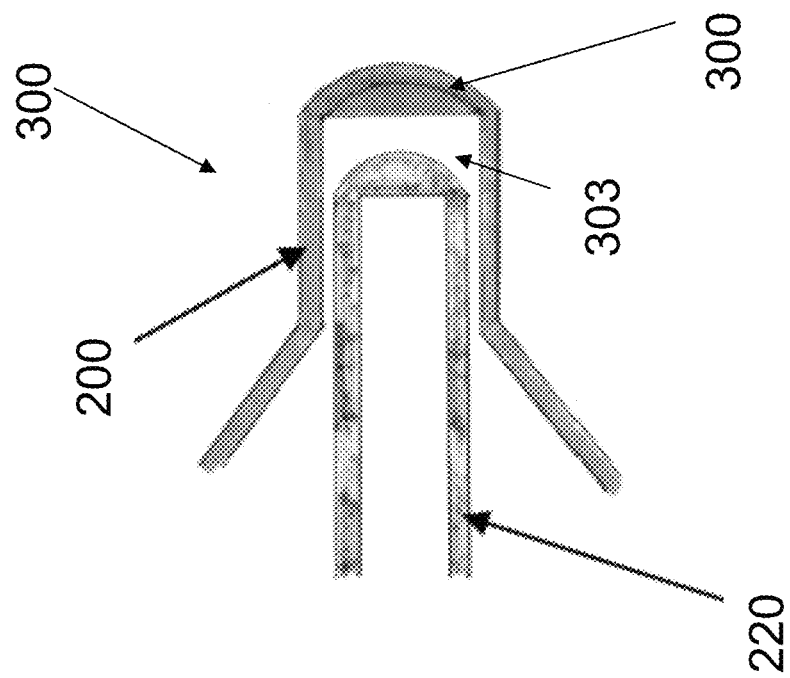
FIG. 7B illustrates an embodiment of a distal tip design for a device for repairing a weakened or fractured bone of the present disclosure.
Figure 7A:
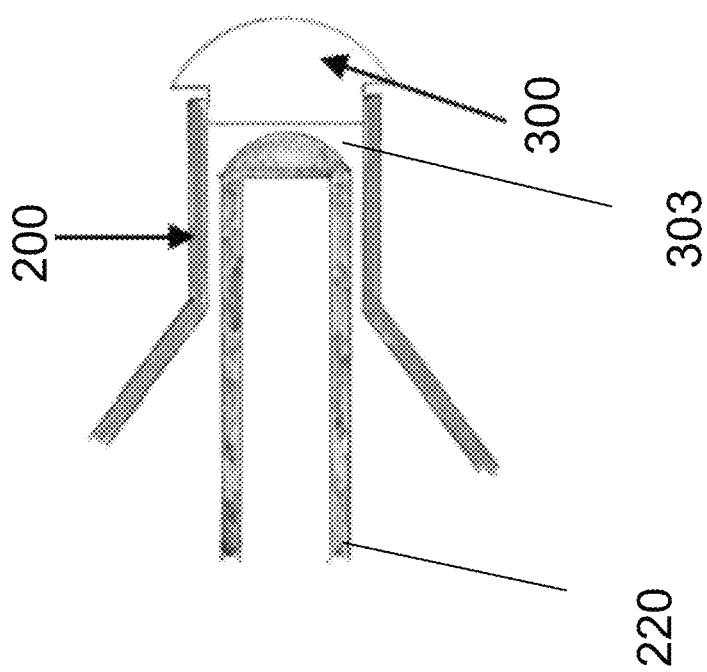
FIG. 7A illustrates an embodiment of a distal tip design for a device for repairing a weakened or fractured bone of the present disclosure.

In reference to FIG. 7A, in some embodiments, the body 302 of the distal cap 300 is formed by the walls of the expandable member 200. In reference to FIG. 7B, in some embodiments, the distal cap 300 may be melt formed from the distal end material of the expandable member 200, while the walls of the expandable member 200 may form the body 302 of the distal cap 300, defining the inner compartment 303. In some embodiments, the end cap may be formed from a separate heat shrink tube. The heat shrink tube may be placed inside the expandable member or external to the expandable member to permit melt forming and/or sealing of the end of the expandable member. In the embodiments shown in FIG. 7A and FIG. 7B, the central tube 220 may be either free floating or may be attached to the distal cap 300.

Figure 8:
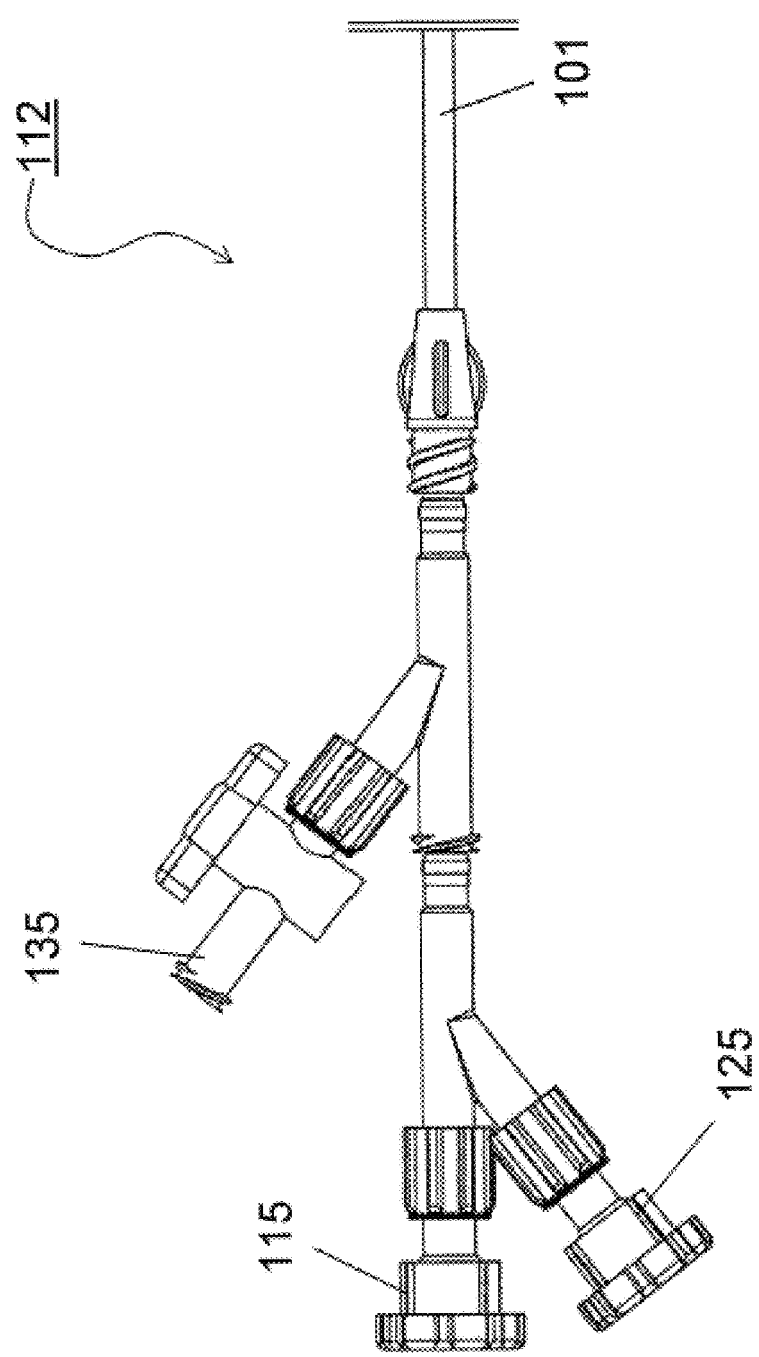
FIG. 8 shows a close up view of an embodiment of a proximal end of a device for repairing a weakened or fractured bone of the present disclosure.

In reference to FIG. 8, a close-up view of an embodiment proximal end 112 of the delivery catheter 101 is illustrated. The proximal end 112 of the flexible delivery catheter 101 includes at least two ports. In the embodiment shown in FIG. 1, the proximal end 112 includes three ports 115, 125, and 135. Port 115 can accept, for example, a light-conducting fiber. In some embodiments, the light-conducting fiber is an optical fiber. In some embodiments, the optical fiber has an outer diameter from about 1 mm to about 3 mm. The optical fiber is sized to pass through an inner lumen of the delivery catheter 101. The optical fiber can be made from any material, such as glass, silicon, silica glass, quartz, sapphire, plastic, combinations of materials, or any other material, and may have any diameter. In some embodiments, the optical fiber is made from a polymethyl methacrylate (PMMA) core with a transparent polymer cladding, often a fluoropolymer such as polytetrafluoroethylene. It should be appreciated that the above-described characteristics and properties of the optical fibers are exemplary and not all embodiments of the present disclosure are intended to be limited in these respects. Port 125 can accept, for example, a syringe housing air or fluid. In some embodiments, port 125 can be used as an air vent during sterilization. Port 135 can accept, for example, a syringe housing a light-sensitive liquid. In some embodiments, the light-sensitive liquid is a liquid monomer. In some embodiments, the syringe maintains a low pressure during the infusion and aspiration of the light-sensitive liquid. In some embodiments, the syringe maintains a low pressure of about 10 atmospheres or less during the infusion and aspiration of the light-sensitive liquid. In some embodiments, the syringe maintains a pressure of between about 1 and about 3 atmospheres.

Light-sensitive liquid can be introduced into the proximal end 112 of the delivery catheter 101 and passes through the inner void 210 of the delivery catheter 101 up into the inner cavity 235 of the expandable member 200 to move the expandable member from a deflated state to an inflated state when the light-sensitive liquid is delivered to the expandable member, in order to form a rigid orthopedic stabilizer. In some embodiments, the light-sensitive liquid is provided as a unit dose. As used herein, the term "unit dose" is intended to mean an effective amount of light sensitive liquid adequate for a single session. By way of example, a unit dose of a light sensitive liquid of the present disclosure for expanding an expandable member of the present disclosure may be defined as enough light-sensitive liquid to expand the expandable member so that the expanded expandable member realigns a fractured bone and/or secures the bone back into an anatomical position. The amount of realigning may vary somewhat from user to user. Thus, a user using a unit dose may have excess light-sensitive liquid left over. It is desirable to provide enough light-sensitive liquid that even the above-average user will have an effective amount of realignment. In some embodiments, a unit dose of a light-sensitive liquid of the present disclosure is contained within a container. In some embodiments, a unit dose of a light-sensitive liquid of the present disclosure is contained in an ampoule. In some embodiments, the expandable member is sufficiently shaped to fit within a space or a gap in a fractured bone. In some embodiments, the light-sensitive liquid can be delivered under low pressure via a standard syringe attached to the port 135. The light-sensitive liquid can be aspirated and reinfused as necessary, allowing for adjustments to the expandable member. These properties allow a user to achieve maximum fracture reduction prior to activating a light source and converting the liquid monomer into a hard polymer.

A light-conducting fiber communicating light from the light source can be introduced into the proximal end 112 of the delivery catheter 101 through port 115 and passes within an inner lumen of the delivery catheter 101 up into the expandable member. In some embodiments, the light source emits frequency that corresponds to a band in the vicinity of 390 nm to 770 nm, the visible spectrum. In some embodiments, the light source emits frequency that corresponds to a band in the vicinity of 410 nm to 500 nm. In some embodiments, the light source emits frequency that corresponds to a band in the vicinity of 430 nm to 450 nm. The light-sensitive liquid remains a liquid monomer until activated by the light-conducting fiber (cures on demand). In some embodiments, the liquid monomer is exposed to an appropriate frequency of light and intensity to cure the monomer inside the expandable member and form a rigid structure. In some embodiments, the liquid monomer is exposed to electromagnetic spectrum that is visible (frequency that corresponds to a band in the vicinity of 390 nm to 770 nm). In some embodiments, the liquid monomer is radiolucent, which permit x-rays to pass through the liquid monomer. Radiant energy from the light source is absorbed and converted to chemical energy to quickly (e.g., cured in about five seconds to about 10 minutes) polymerize the monomer. This cure affixes the expandable member in an expanded shape. A cure may refer to any chemical, physical, and/or mechanical transformation that allows a composition to progress from a form (e.g., flowable form) that allows it to be delivered through the inner void in the delivery catheter 101, into a more permanent (e.g., cured) form for final use in vivo. For example, "curable" may refer to uncured composition, having the potential to be cured in vivo (as by catalysis or the application of a suitable energy source), as well as to a composition in the process of curing (e.g., a composition formed at the time of delivery by the concurrent mixing of a plurality of composition components).

Additives may be included in light-sensitive liquids, including, but not limited to, drugs (for example, antibiotics), proteins (for example, growth factors) or other natural or synthetic additives (for example, radiopaque or ultrasonically active materials). In some embodiments, the viscosity of the light-sensitive liquid has a viscosity of about 1000 cP or less. In some embodiments, the light-sensitive liquid has a viscosity ranging from about 650 cP to about 450 cP. The expandable member may be inflated, trial fit and adjusted as many times as a user wants with the light-sensitive liquid, up until the light source is activated, when the polymerization process is initiated. Because the light-sensitive liquid has a liquid consistency and is viscous, the light-sensitive liquid may be delivered using low pressure delivery and high pressure delivery is not required, but may be used.

In some embodiments, a contrast material may be added to the light-sensitive liquid without significantly increasing the viscosity. Contrast materials include, but are not limited to, bismouth subcarbonate, barium sulfate, bismuth subcarbonate, tantalum, or other contrast materials known in the art. The light-sensitive liquid can be introduced into the proximal end of the delivery catheter and passes within the inner void of the delivery catheter up into an inner cavity of the expandable member to change a thickness of the expandable member without changing a width or depth of the expandable member. In some embodiments, the light-sensitive liquid is delivered under low pressure via the syringe attached to the port. The light-sensitive liquid can be aspirated and reinfused as necessary, allowing for thickness adjustments to the expandable body prior to activating the light source and converting the liquid monomer into a hard polymer. Low viscosity allows filling of the intramedullary implant through a very small delivery system.

One or more radiopaque markers or bands may be placed at various locations along the expandable member 200 and/or the delivery catheter 101. A radiopaque ink bead may be placed at a distal end of the expandable member for alignment of the apparatus during fluoroscopy. The one or more radiopaque bands and radiopaque ink bead, using radiopaque materials such as bismouth subcarbonate, barium sulfate, tantalum, or other materials known to increase radiopacity, allows a medical professional to view the apparatus using fluoroscopy techniques. The one or more radiopaque bands also provide visibility during inflation of the expandable member to determine the precise positioning of the expandable member during placement and inflation.

In some embodiments, the expandable member 200 can have a length greater than about 300 mm and a diameter greater than about 20 mm. In such embodiments, there is the potential that during the curing of the light-sensitive liquid, a far distal area 214 of the expandable member 200 will exhibit a shrinkage upon cure of about 2 to about 3 percent, while a proximal area 212 of the expandable member 200 is being cured. In some embodiments, to prevent this from transpiring, the central tube 220 of the expandable member 200 can be pressurized by virtue of the infusion of either air or other fluids (saline, water) through port 125 at the proximal end 112 of the delivery catheter 101. The infusion will cause internal diameter pressure against the light-sensitive liquid contained within the inner cavity 235 of the expandable member 200 so that during the curing process, the pressure keeps the light-sensitive liquid pressurized, and up in contact with inner surface 230 of the expandable member 200. When the light-conducting fiber is inserted within the central tube 220 and the light-sensitive liquid is infused, the extra space is pressed down on the central tube 220. In some embodiments, the central tube 220 is rigid and heat resistant so it does not deform, collapse or expand, due to the light energy from the light conducting fiber to facilitate easy removal of the light conducting fiber after the cure cycle. In some embodiments, an expandable member of the present disclosure has a diameter ranging from about 4 mm to about 30 mm. In some embodiments, an expandable member of the present disclosure has a length ranging from about 20 mm to about 500 mm. An expandable member of the present disclosure may be round, flat, cylindrical, oval, rectangular or any desired shape for a given application. In some embodiments, an expandable member of the present disclosure has a diameter of about 4 mm and a length of about 30 mm. In some embodiments, an expandable member of the present disclosure has a diameter of about 5 mm and a length of about 40 mm. In some embodiments, an expandable member of the present disclosure has a diameter of about 6 mm and a length of about 30 mm. In some embodiments, an expandable member of the present disclosure has a diameter of about 6 mm and a length of about 40 mm. In some embodiments, an expandable member of the present disclosure has a diameter of about 6 mm and a length of about 50 mm. In some embodiments, an expandable member of the present disclosure has a diameter of about 7 mm and a length of about 30 mm. In some embodiments, an expandable member of the present disclosure has a diameter of about 7 mm and a length of about 40 mm. In some embodiments, an expandable member of the present disclosure has a diameter of about 4 mm to about 20 mm and a length of about 30 mm to about 280 mm.

In some embodiments, an outer surface of an expandable member of the present disclosure is resilient. In some embodiments, an outer surface of an expandable member of the present disclosure is substantially even and smooth. In some embodiments, an outer surface of an expandable member of the present disclosure is not entirely smooth and may have some small bumps or convexity/concavity along the length. In some embodiments, an outer surface of an expandable member of the present disclosure may have ribs, ridges, projections, bumps or other shapes. In some embodiments, the ribs, ridges, projections, bumps, or other shapes on the rough or uneven outer surface of the expandable member improve penetration of the at least one fastener into the expandable member. In some embodiments, the ribs, ridges, projections, bumps, or other shapes on the rough or uneven outer surface of the expandable member improve penetration of the at least one fastener into the expandable member anywhere along a length of the expandable member. In some embodiments, the ribs, ridges, projections, bumps, or other shapes on the rough or uneven outer surface of the expandable member increase friction between the outer surface of the expandable member and the at least one fastener so as to reduce slippage of the at least one fastener as the at least one fastener is driven towards the outer surface of the expandable member. In some embodiments, the ribs, ridges, projections, bumps, or other shapes on the rough or uneven outer surface of the expandable member interacts with a threaded portion of the at least one fastener so as to improve penetration and fastening of the at least one fastener into the expandable member. In some embodiments, the ribs, ridges, projections, bumps, or other shapes on the rough or uneven outer surface of the expandable member interact with a tip of the at least one fastener to improve the wedge ability of the tip of the fastener so as to decrease the driving force needed to penetrate the expandable member. In some embodiments, an outer surface of an expandable member of the present disclosure has an uneven geometry. In some embodiments, an outer surface of an expandable member of the present disclosure has a textured surface which provides one or more ridges that allow grabbing. In some embodiments, the one or more ridges on the textured surface of the expandable member allow grabbing of the at least one fastener so as to improve the penetration of the at least one fastener into the expandable member. In some embodiments, the one or more ridges on the textured surface of the expandable member allow grabbing of bone so as to improve adhesion between the expandable member and bone as regenerating bone grows onto the outer surface of the expandable member. In some embodiments, abrasively treating an outer surface of an expandable member of the present disclosure for example via chemical etching or air propelled abrasive media improves the connection and adhesion between the outer surface of the expandable member and a bone. The surfacing may significantly increase the amount of surface area that comes in contact with the bone resulting in a stronger grip. In some embodiments, the textured surface promotes bone growth onto the expandable member. In some embodiments, the textured surface promotes bone growth of regenerating bone onto the outer surface of the expandable member by grabbing the regenerating bone as it grows. In some embodiments, an expandable member of the present disclosure is made by extruding material into a tube shape, and then forming the tube into a balloon. When forming the tube into the balloon, the balloon can be, for example, pre-stamped or milled to include a desired design, desired shape or surface modification. Then, the tube is heated and radially expanded via compressed air for a specific amount of time. The formed balloon is cooled and includes the desired design, desired shape or surface modification.

In some embodiments, an expandable member of the present disclosure has an outer surface that is coated with materials such as drugs, bone glue, proteins, growth factors, or other coatings. For example, after a minimally invasive surgical procedure an infection may develop in a patient, requiring the patient to undergo antibiotic treatment. An antibiotic drug may be added to an outer surface of an expandable member of the present disclosure to prevent or combat a possible infection. Proteins, such as, for example, bone morphogenic protein or other growth factors have been shown to induce the formation of cartilage and bone. In some embodiments, a growth factor is added to an outer surface of an expandable member of the present disclosure to help induce the formation of new bone. In some embodiments, as the formation of new bone is induced the new bone interacts with a textured outer surface of the expandable member so that new bone is formed onto the textured outer surface of the expandable member. Due to the lack of thermal egress of light-sensitive liquid in an expandable member of the present disclosure, the effectiveness and stability of the coating is maintained.

In some embodiments, a stiffness of any of the expandable member of the present disclosure can be increased due to the presence of external stiffening members or internal stiffening members. In some embodiments, a wrapping, sheathing or an attachment of Nitinol or other metallic memory-type metal piece(s) are aligned in a longitudinal fashion, with multiple rods being placed circumferentially around the expandable member so as to have these metallic pieces change their configuration under a temperature change. In some embodiments, an inner surface of the metallic pieces (those surfaces that are in contact with the external circumferential surface of the intramedullary implant) are polished to increase internal reflection of the light from the light-conducting fiber. The metallic pieces are designed to be load-bearing shapes. In some embodiments, the metallic pieces have a low profile and can handle large loads. In some embodiments, metallic pieces may be positioned on the external circumferential surface of an expandable member. The metallic pieces can be aligned in a longitudinal fashion, circumferentially around the expandable member and can be interconnected with one another via connecting means such as wires. The wires will help hold the longitudinal metallic pieces in position. In some embodiments, the metallic pieces expand to increase the strength of the hardened expandable member. In some embodiments, the metallic pieces contract to increase the strength of the hardened expandable member. In some embodiments, metallic pieces are positioned on an internal circumferential surface of an expandable member. In some embodiments, two metallic memory-type metal wires, such as Nitinol, are positioned within an expandable member. Heat from a light-conducting fiber makes the metal wires get smaller, tensioning the hardened expandable member. In some embodiments, heat from a light-conducting fiber and reaction with the polymerization process, makes the metal wires get smaller, tensioning the hardened expandable member. In some embodiments, an expandable member is wrapped with a plurality of flat metallic plates that move into a corrugated or other shape upon a temperature change to increase the strength of the previously flat metal plate into a shape capable of handling a load. In some embodiments, the metals are rectangular, semicircular, hexagonal, or triangular in section, although not all embodiments are limited to these shapes.

An expandable member typically does not have any valves. One benefit of having no valves is that the expandable member may be inflated or deflated as much as necessary to assist in the fracture reduction and placement. Another benefit of the expandable member having no valves is the efficacy and safety of the implant. Since there is no communication passage of light-sensitive liquid to the body there cannot be any leakage of liquid because all the liquid is contained within the expandable member. In some embodiments, a permanent seal is created between the expandable member that is both hardened and affixed prior to the delivery catheter 101 being removed. The expandable member may have valves, as all of the embodiments are not intended to be limited in this manner.

In some embodiments, an expandable member of the present disclosure includes a pathway sufficiently designed for passing a cooling medium. Once the expandable member is expanded, a cooling media may be delivered within (via an internal lumen) or around (via external tubing) the expandable member in order to prevent the possibility of overheating. Medium used for cooling includes, but is not limited to, gases, liquids and combinations thereof. Examples of gases include, but are not limited to, inert gases and air. Examples of liquids include, but are not limited to, water, saline, saline-ice mixtures, liquid cryogen. In some embodiments, the cooling media is water. The cooling media can be delivered to the expandable member at room temperature or at a cooled temperature. In some embodiments, the cooling media improves the numerical aperture between that of the light-conducting fiber and the inner lumen for the light-conducting fiber because any air existing between the light-conducting fiber and the material of the expandable member is taken away so as to improve light transmission. Therefore, light will be transmitted from the light-conducting fiber to the light-sensitive liquid through the cooling medium as opposed to through air. In some embodiments, the cooling media transmitted through the inner lumen of the expandable member takes away extraneous heat. In some embodiments, no cooling media is used.

In some embodiments, a light-conducting fiber can be introduced into the inner lumen of the expandable member and activated to cure the light-sensitive liquid, while a cooling medium may flow through the inner lumen and out the distal end of the expandable member.

In reference to FIG. 9A, FIG. 9B, FIG. 9C, FIG. 9D and FIG. 9E, embodiment methods for implanting an intramedullary implant of the present disclosure within the intramedullary space of a weakened or fractured bone are illustrated.

A minimally invasive incision (not shown) may be made through the skin of the patient's body to expose a fractured bone 902. The incision may be made at the proximal end or the distal end of the fractured bone 902 to expose the bone surface. Once the bone 902 is exposed, it may be necessary to retract some muscles and tissues that may be in view of the bone 902. As shown in FIG. 9A, an access hole 910 may be formed in the bone by drilling or other methods known in the art. In some embodiments, the access hole 910 has a diameter of about 4 mm to about 7 mm. In some embodiments, the access hole 910 has a diameter of about 9 mm.

The access hole 910 extends through a hard compact (cortical) outer layer 920 of the bone into the relatively porous inner or cancellous tissue 925. For bones with marrow, the medullary material should be cleared from the medullary cavity prior to insertion of the inventive device. Marrow is found mainly in the flat bones such as hip bone, breast bone, skull, ribs, vertebrae and shoulder blades, and in the cancellous material at the proximal ends of the long bones like the femur and humerus. Once the medullary cavity is reached, the medullary material including air, blood, fluids, fat, marrow, tissue and bone debris should be cleared or loosened to form a void. The void is defined as a hollowed out space, wherein a first position defines the most distal edge of the void with relation to the penetration point on the bone, and a second position defines the most proximal edge of the void with relation to the penetration site on the bone. The bone may be hollowed out sufficiently to have the medullary material of the medullary cavity up to the cortical bone removed. There are many methods for removing the medullary material that are known in the art and within the spirit and scope on the presently disclosed embodiments. Methods include those described in U.S. Pat. No. 4,294,251 entitled "Method of Suction Lavage," U.S. Pat. No. 5,554,111 entitled "Bone Cleaning and Drying system," U.S. Pat. No. 5,707,974 entitled "Apparatus for Preparing the Medullary Cavity," U.S. Pat. No. 6,478,751 entitled "Bone Marrow Aspiration Needle," and U.S. Pat. No. 6,958,252 entitled "Apparatus for Extracting Bone Marrow."

A guidewire (not shown) may be introduced into the bone 902 via the access hole 910 and placed between bone fragments 904 and 906 of the bone 902 to cross the location of a fracture 905. The guidewire may be delivered into the lumen of the bone 902 and may cross the location of the break 905 so that the guidewire spans multiple sections of bone fragments. As shown in FIG. 9B, the expandable member 200 of the delivery catheter 101 for repairing a fractured bone, which is constructed and arranged to accommodate the guidewire, is delivered over the guidewire to the site of the fracture 905 and spans the bone fragments 904 and 906 of the bone 902. Once the expandable member 200 is in place, the guidewire may be removed. The location of the expandable member 200 may be determined using at least one radiopaque marker 990 which is detectable from the outside or the inside of the bone 902. Once the expandable member 200 is in the correct position within the fractured bone 902, a delivery system which contains a light-sensitive liquid is attached to the port 195. The light-sensitive liquid is then infused through the inner void 210 in the delivery catheter 101 and enters the inner cavity 295 of the expandable member 200. This addition of the light-sensitive liquid within the expandable member 200 causes the expandable member 200 to expand, as shown in FIG. 9C. As the expandable member 200 is expanded, the fracture 905 is reduced. Unlike traditional implants, such as rods, that span the fracture site, the expandable member 200 of the present disclosure does more than provide longitudinal strength to both sides of the fractured bone. In some embodiments, the expandable member 200 having the design can be a spacer for reducing the fracture and for holding the fractured and compressed bones apart at the point of the collapsed fracture.

Once orientation of the bone fragments 904 and 906 are confirmed to be in a desired position, the light-sensitive liquid may be hardened within the expandable member 200, as shown in FIG. 9D, such as by illumination with a visible emitting light source. In some embodiments, during the curing step, a syringe housing a cooling media may be attached to the proximal end of the delivery catheter and continuously delivered to the expandable member 200. The cooling media can be collected by connecting tubing to the distal end of the inner lumen and collecting the cooling media via the second distal access hole. After the light-sensitive liquid has been hardened, the light source may be removed from the device. Alternatively, the light source may remain in the expandable member 200 to provide increased rigidity.

Figure 9E:
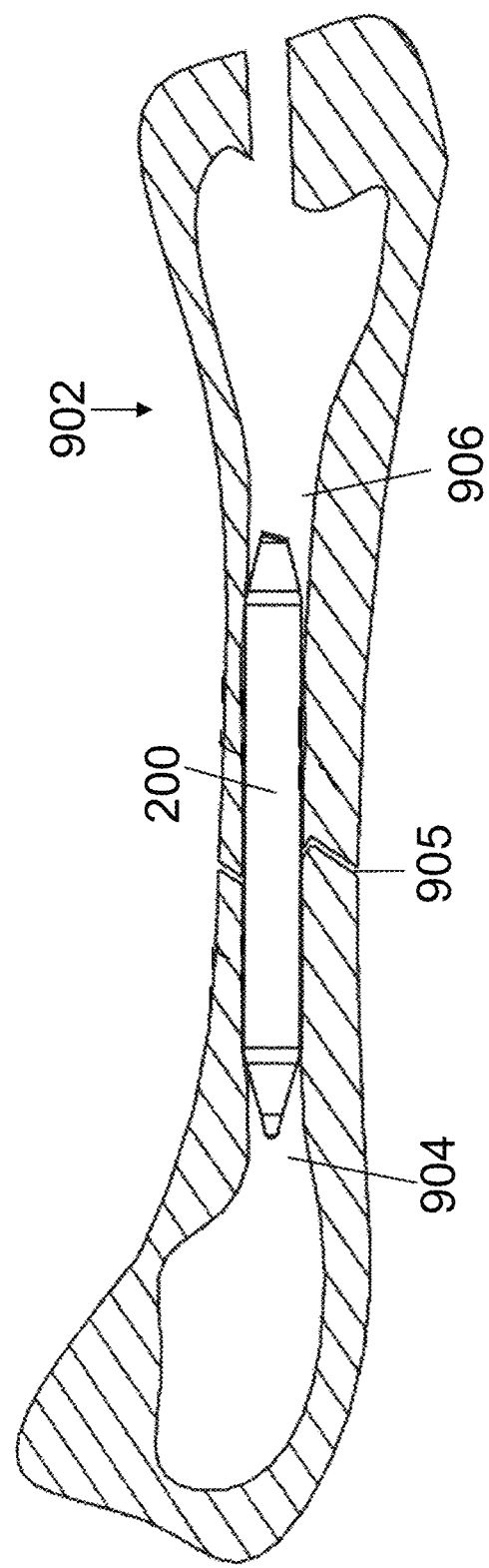

FIG. 9E shows an embodiment of a bone fixation device in a cavity of a bone after being separated from an introducer. For example, the expandable member 200 once hardened, may be released from the delivery catheter 101 to form a photodynamic bone fixation device inside the intramedullary cavity of the bone 902.

In some embodiments, a device for internal bone fixation includes an delivery catheter having a proximal end and a distal end, an expandable member having a proximal region and a distal region, wherein the expandable member is relesably attached about the distal end of the delivery catheter at its proximal region, and a distal cap attached to the distal region of the expandable member to seal the expandable member.

In some embodiments, a device for internal bone fixation includes an delivery catheter having a proximal end and a distal end, a distal cap positioned distally of the delivery catheter, an inner lumen extending through the delivery catheter past the distal end of the delivery catheter for insertion into the distal cap, and an expandable member releasably attached about the distal end of the delivery catheter at its proximal region and is sealed by the distal cap at its distal region.

In some embodiments, a system for internal bone fixation includes an delivery catheter having a proximal end and a distal end; an expandable member having a proximal region and a distal region, wherein the expandable member is relesably attached about the distal end of the delivery catheter at its proximal region, and a distal cap attached to the distal region of the expandable member to seal the expandable member; a light conducting fiber; and a light cure adhesive, wherein the delivery catheter has an inner void for passage of a light-sensitive liquid into the expandable member to expand the expandable member and an inner lumen for passage of a light conducting fiber into the expandable member to cure the light-sensitive liquid inside the expandable member.

In some embodiments, a method for internal bone fixation that includes advancing to a fractured bone a device that includes an delivery catheter having a proximal end and a distal end; an expandable member having a proximal region and a distal region, wherein the expandable member is relesably attached about the distal end of the delivery catheter at its proximal region, and a distal cap attached to the distal region of the expandable member to seal the expandable member; positioning the expandable member of the device within an intramedullary cavity of the fractured bone; expanding the expandable member with a light-sensitive liquid; and curing the light-sensitive liquid within the expandable member.

In some embodiments, a device for bone fixation includes a delivery catheter comprising an outer tube and an inner tube disposed within the outer tube and extending beyond the outer tube; an expandable member having a proximal region and a distal region, the expandable member being relesably attached about a distal end of the delivery catheter at the proximal region of the expandable member, and a distal cap attached to the distal region of the expandable member to seal the expandable member; and an inner compartment in the distal region of the expandable member, the inner compartment being configured to receive the inner tube and enable movement of the inner tube within the inner compartment.

In some embodiments, a system for bone fixation includes a delivery catheter having a proximal end and a distal end; an expandable member having a proximal region and a distal region, wherein the expandable member is releasably attached about the distal end of the delivery catheter at the proximal region of the expandable member; a distal cap attached to the distal region of the expandable member to seal the expandable member; a light conducting fiber; and a light-sensitive liquid; wherein the delivery catheter has an inner void for passage of a light-sensitive liquid into the expandable member to expand the expandable member and an inner lumen for passage of the light conducting fiber into the expandable member to cure the light-sensitive liquid inside the expandable member.

In some embodiments, a method for bone fixation includes advancing to a fractured bone a device comprising a delivery catheter having a proximal end and a distal end; an expandable member having a proximal region and a distal region, wherein the expandable member is attached about the distal end of the delivery catheter at the proximal region of the expandable member; and a distal cap attached to the distal region of the expandable member to seal the expandable member; positioning the expandable member within an intramedullary cavity of the fractured bone; expanding the expandable member with a light-sensitive liquid; and curing the light-sensitive liquid within the expandable member.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, and as fall within the scope of the appended claims

What is claimed is:

1. A device for bone fixation comprising:
   a delivery catheter comprising an outer tube and an inner tube, the inner tube disposed within the outer tube and the inner tube extending beyond the outer tube;
   an expandable member having a proximal region and an open distal region, the expandable member being releasably attached about a distal end of the delivery catheter at the proximal region of the expandable member; and a distal cap attached to the open distal region of the expandable member to seal off the open distal region of the expandable member; and an inner compartment defined by a body of the distal cap, wherein a distal end of the inner tube is inserted into the inner compartment defined by the body of the distal cap, and the inner compartment is sized such that the inner tube is freely moveable within the inner compartment in a radial direction.

2. The device of claim 1 wherein the body of the distal cap is a tubular body defining the inner compartment for receiving and accommodating the inner tube, so as to stabilize and minimize bowing of the inner tube during operation.

3. The device of claim 2 wherein the delivery catheter includes:

an inner void between the inner tube and the outer tube and in fluid communication with an inner cavity within the expandable member to deliver a light-sensitive liquid into the inner cavity of the expandable member, and an inner lumen extending along the inner tube for passing a light-conducting fiber into the expandable member to cure the light sensitive liquid inside the inner cavity of the expandable member.

4. The device of claim 3 further comprising a seal formed between the inner lumen and the inner compartment.

5. The device of claim 1 wherein the inner tube is freely moveable within the inner compartment in the radial direction and a longitudinal direction.

6. The device of claim 1 wherein the inner tube includes a plug insertable into the inner compartment of the distal cap.

7. The device of claim 1 wherein the distal cap includes a slotted wall into which the expandable member is inserted.

8. The device of claim 1 wherein the distal cap includes a recessed outer surface to which the expandable member is attached.

9. The device of claim 1 wherein the expandable member is inserted into the inner compartment defined by the distal cap, the distal cap having an inner surface circumferentially attached to the distal region of an outer surface of the expandable member to seal the expandable member.

10. A system for bone fixation comprising:

a delivery catheter having a proximal end and a distal end and an inner tube extending beyond an outer tube;

an expandable member having a proximal region and an open distal region, wherein the expandable member is releasably attached about the distal end of the delivery catheter at the proximal region of the expandable member;

a light-sensitive liquid;

a distal cap attached to the open distal region of the expandable member to seal off the open distal region of the expandable member; and an inner compartment defined by a body of the distal cap, wherein a distal end of the inner tube is inserted into the inner compartment defined by the body of the distal cap, and the inner compartment is sized such that the inner tube is freely moveable within the inner compartment in a radial direction; and a light conducting fiber;

wherein the delivery catheter has an inner void for passage of the light-sensitive liquid into the expandable member to expand the expandable member and an inner lumen for passage of the light conducting fiber into the expandable member to cure the light-sensitive liquid inside the expandable member.

11. The system of claim 10, wherein the distal cap is configured to prevent the flow of the light-sensitive liquid from inside to outside of the expandable member and the ingress of bodily fluids inside the expandable member.

12. The system of claim 10 wherein the inner tube is free floating within the inner compartment of the distal cap.

13. The system of claim 10 wherein the inner tube includes a plug insertable into the inner compartment of the distal cap.

14. The system of claim 10 wherein the distal cap includes a slotted wall into which the expandable member is inserted.

15. The system of claim 10 wherein the distal cap includes a recessed outer surface to which the expandable member is attached.

16. The system of claim 10 wherein the expandable member is inserted into the inner compartment defined by the distal cap, the distal cap having an inner surface circumferentially attached to the distal region of an outer surface of the expandable member to seal the expandable member.

\* \* \* \* \*